United States Patent
Shanley

(10) Patent No.: US 8,361,537 B2
(45) Date of Patent: Jan. 29, 2013

(54) EXPANDABLE MEDICAL DEVICE WITH BENEFICIAL AGENT CONCENTRATION GRADIENT

(75) Inventor: John F. Shanley, Redwood City, CA (US)

(73) Assignee: Innovational Holdings, LLC

( * ) Notice: Subject to any disclaimer, the term of this patent is extended or adjusted under 35 U.S.C. 154(b) by 1156 days.

(21) Appl. No.: 11/925,344

(22) Filed: Oct. 26, 2007

(65) Prior Publication Data

US 2008/0097581 A1    Apr. 24, 2008

Related U.S. Application Data

(63) Continuation of application No. 10/857,201, filed on May 27, 2004, now abandoned, which is a continuation-in-part of application No. 10/668,430, filed on Sep. 22, 2003, said application No. 10/857,201 is a continuation-in-part of application (Continued)

(51) Int. Cl.
*A61L 33/00* (2006.01)
*B05D 3/02* (2006.01)
*A61F 2/06* (2006.01)

(52) U.S. Cl. ...... 427/2.24; 427/2.1; 427/2.25; 623/1.42; 623/1.44; 623/1.46

(58) Field of Classification Search .......... 427/2.1–2.31; 623/1.15–1.46
See application file for complete search history.

(56) References Cited

U.S. PATENT DOCUMENTS

| | | |
|---|---|---|
| 3,657,744 A | 4/1972 | Ersek |
| 4,300,244 A | 11/1981 | Bukros |
| 4,531,936 A | 7/1985 | Gordon |
| 4,542,025 A | 9/1985 | Tice et al. |
| 4,580,568 A | 4/1986 | Gianturco |
| 4,650,466 A | 3/1987 | Luther |
| 4,733,665 A | 3/1988 | Palmaz |
| 4,739,762 A | 4/1988 | Palmaz |
| 4,776,337 A | 10/1988 | Palmaz |
| 4,800,882 A | 1/1989 | Gianturco |
| 4,824,436 A | 4/1989 | Wollinsky |

(Continued)

FOREIGN PATENT DOCUMENTS

CA    2234787 A1    4/1998
CA    2323358 C     10/1999

(Continued)

OTHER PUBLICATIONS

Japanese Office Action dated Oct. 19, 2010 in Japanese Patent Application No. 2002-535586.

(Continued)

*Primary Examiner* — Timothy Meeks
*Assistant Examiner* — Cachet Sellman

(57) ABSTRACT

An expandable medical device has a plurality of elongated struts joined together to form a substantially cylindrical device, which is expandable from a cylinder having a first diameter to a cylinder having a second diameter. At least one of the plurality of struts includes at least one opening extending at least partially through a thickness of the strut. A beneficial agent is loaded into the opening within the strut in layers to achieve desired temporal release kinetics of the agent. Alternatively, the beneficial agent is loaded in a shape which is configured to achieve the desired agent delivery profile. A wide variety of delivery profiles can be achieved including zero order, pulsatile, increasing, decrease, sinusoidal, and other delivery profiles.

5 Claims, 10 Drawing Sheets

Related U.S. Application Data

No. 10/253,020, filed on Sep. 23, 2002, now Pat. No. 7,208,011, which is a continuation-in-part of application No. 09/948,989, filed on Sep. 7, 2001, now Pat. No. 7,208,010, and a continuation-in-part of application No. 09/688,092, filed on Oct. 16, 2000, now abandoned, which is a continuation-in-part of application No. 09/183,555, filed on Oct. 29, 1998, now Pat. No. 6,241,762.

(60) Provisional application No. 60/412,489, filed on Sep. 20, 2002, provisional application No. 60/314,259, filed on Aug. 20, 2001, provisional application No. 60/079,881, filed on Mar. 30, 1998.

(56) References Cited

U.S. PATENT DOCUMENTS

| | | |
|---|---|---|
| 4,834,755 A | 5/1989 | Silvestrini et al. |
| 4,955,878 A | 9/1990 | See et al. |
| 4,957,508 A | 9/1990 | Kaneko et al. |
| 4,960,790 A | 10/1990 | Stella et al. |
| 4,969,458 A | 11/1990 | Wiktor |
| 4,989,601 A | 2/1991 | Marchosky et al. |
| 4,990,155 A | 2/1991 | Wilkoff et al. |
| 4,994,071 A | 2/1991 | MacGregor |
| 5,019,090 A | 5/1991 | Pinchuk |
| 5,049,132 A | 9/1991 | Shaffer et al. |
| 5,053,048 A | 10/1991 | Pinchuk |
| 5,059,166 A | 10/1991 | Fischell et al. |
| 5,059,178 A | 10/1991 | Ya et al. |
| 5,059,211 A | 10/1991 | Stack et al. |
| 5,078,726 A | 1/1992 | Kreamer |
| 5,092,841 A | 3/1992 | Spears |
| 5,171,217 A | 12/1992 | March et al. |
| 5,171,262 A | 12/1992 | MacGregor |
| 5,176,617 A | 1/1993 | Fischell et al. |
| 5,195,984 A | 3/1993 | Schatz |
| 5,197,978 A | 3/1993 | Hess |
| 5,213,580 A | 5/1993 | Slepian et al. |
| 5,234,456 A | 8/1993 | Silvestrini |
| 5,242,399 A | 9/1993 | Lau et al. |
| 5,286,254 A | 2/1994 | Shapland et al. |
| 5,292,512 A | 3/1994 | Schaefer et al. |
| 5,304,121 A | 4/1994 | Sahatjian |
| 5,314,688 A | 5/1994 | Kauffman et al. |
| 5,342,621 A | 8/1994 | Eury |
| 5,344,426 A | 9/1994 | Lau et al. |
| 5,380,299 A | 1/1995 | Fearnot et al. |
| 5,383,892 A | 1/1995 | Cardon et al. |
| 5,383,928 A | 1/1995 | Scott et al. |
| 5,403,858 A | 4/1995 | Bastard et al. |
| 5,407,683 A | 4/1995 | Shively |
| 5,415,869 A | 5/1995 | Straubinger et al. |
| 5,419,760 A | 5/1995 | Narciso |
| 5,439,446 A | 8/1995 | Barry |
| 5,439,686 A | 8/1995 | Desai et al. |
| 5,441,515 A | 8/1995 | Khosravi et al. |
| 5,441,745 A | 8/1995 | Presant et al. |
| 5,443,496 A | 8/1995 | Schwartz et al. |
| 5,443,497 A | 8/1995 | Venbrux |
| 5,443,500 A | 8/1995 | Sigwart |
| 5,447,724 A | 9/1995 | Helmus et al. |
| 5,449,373 A | 9/1995 | Pinchasik et al. |
| 5,449,513 A | 9/1995 | Yokoyama et al. |
| 5,457,113 A | 10/1995 | Cullinan et al. |
| 5,460,817 A | 10/1995 | Langley et al. |
| 5,462,866 A | 10/1995 | Wang |
| 5,464,450 A | 11/1995 | Buscemi et al. |
| 5,464,650 A | 11/1995 | Berg et al. |
| 5,472,985 A | 12/1995 | Grainger et al. |
| 5,473,055 A | 12/1995 | Mongelli et al. |
| 5,499,373 A | 3/1996 | Richards et al. |
| 5,534,287 A | 7/1996 | Lukic |
| 5,545,208 A | 8/1996 | Wolff et al. |
| 5,545,210 A | 8/1996 | Hess et al. |
| 5,545,569 A | 8/1996 | Grainger et al. |
| 5,556,413 A | 9/1996 | Lam |
| 5,578,075 A | 11/1996 | Dayton |
| 5,593,434 A | 1/1997 | Williams |
| 5,595,722 A | 1/1997 | Grainger et al. |
| 5,599,844 A | 2/1997 | Grainger et al. |
| 5,605,696 A | 2/1997 | Eury et al. |
| 5,607,442 A | 3/1997 | Fischell et al. |
| 5,609,629 A | 3/1997 | Fearnot et al. |
| 5,616,608 A | 4/1997 | Kinsella et al. |
| 5,617,878 A | 4/1997 | Taheri |
| 5,618,299 A | 4/1997 | Khosravi et al. |
| 5,628,787 A | 5/1997 | Mayer |
| 5,643,314 A | 7/1997 | Carpenter et al. |
| 5,665,591 A | 9/1997 | Sonenshein et al. |
| 5,674,278 A | 10/1997 | Boneau |
| 5,697,971 A | 12/1997 | Fischell et al. |
| 5,713,949 A | 2/1998 | Jayaranman |
| 5,716,981 A | 2/1998 | Hunter et al. |
| 5,725,548 A | 3/1998 | Jayaraman |
| 5,725,549 A | 3/1998 | Lam |
| 5,733,330 A | 3/1998 | Cox |
| 5,741,293 A | 4/1998 | Wijay |
| 5,759,192 A | 6/1998 | Saunders |
| 5,769,883 A | 6/1998 | Buscemi et al. |
| 5,770,609 A | 6/1998 | Grainger et al. |
| 5,773,479 A | 6/1998 | Grainger et al. |
| 5,776,181 A | 7/1998 | Lee et al. |
| 5,776,184 A * | 7/1998 | Tuch .............................. 623/1.11 |
| 5,797,898 A | 8/1998 | Santini et al. |
| 5,807,404 A | 9/1998 | Richter |
| 5,811,447 A | 9/1998 | Kunz et al. |
| 5,817,152 A | 10/1998 | Birdsall et al. |
| 5,824,045 A | 10/1998 | Alt |
| 5,824,049 A | 10/1998 | Ragheb et al. |
| 5,827,322 A | 10/1998 | Williams |
| 5,837,008 A | 11/1998 | Berg et al. |
| 5,843,117 A | 12/1998 | Alt et al. |
| 5,843,120 A | 12/1998 | Israel et al. |
| 5,843,175 A | 12/1998 | Frantzen |
| 5,853,419 A | 12/1998 | Imran |
| 5,855,600 A | 1/1999 | Alt |
| 5,868,781 A | 2/1999 | Killion |
| 5,873,904 A | 2/1999 | Ragheb et al. |
| 5,876,419 A | 3/1999 | Carpenter et al. |
| 5,922,020 A | 7/1999 | Klein et al. |
| 5,922,021 A | 7/1999 | Jang |
| 5,928,916 A | 7/1999 | Keogh |
| 5,935,506 A | 8/1999 | Schmitz et al. |
| 5,945,456 A | 8/1999 | Grainger et al. |
| 5,964,798 A | 10/1999 | Imran |
| 5,968,092 A | 10/1999 | Buscemi et al. |
| 5,972,027 A | 10/1999 | Johnson |
| 5,976,182 A | 11/1999 | Cox |
| 5,980,551 A | 11/1999 | Summers et al. |
| 5,980,972 A | 11/1999 | Ding |
| 5,981,568 A | 11/1999 | Kunz et al. |
| 5,984,957 A | 11/1999 | Laptewicz, Jr. et al. |
| 5,992,769 A | 11/1999 | Wise |
| 5,994,341 A | 11/1999 | Hunter et al. |
| 6,007,517 A | 12/1999 | Anderson |
| 6,017,363 A | 1/2000 | Hojeibane |
| 6,019,789 A | 2/2000 | Dinh et al. |
| 6,022,371 A | 2/2000 | Killion |
| 6,030,414 A | 2/2000 | Taheri |
| 6,071,305 A | 6/2000 | Brown et al. |
| 6,083,258 A | 7/2000 | Yadav |
| 6,096,070 A | 8/2000 | Ragheb et al. |
| 6,123,861 A | 9/2000 | Santini et al. |
| 6,156,062 A | 12/2000 | McGuiness |
| 6,171,609 B1 | 1/2001 | Kunz |
| 6,203,569 B1 | 3/2001 | Wijay |
| 6,206,915 B1 | 3/2001 | Fagan et al. |
| 6,239,118 B1 | 5/2001 | Schatz et al. |
| 6,240,616 B1 | 6/2001 | Yan |
| 6,241,762 B1 | 6/2001 | Shanley |
| 6,245,104 B1 * | 6/2001 | Alt .............................. 427/2.25 |
| 6,249,952 B1 | 6/2001 | Ding |

| | | |
|---|---|---|
| 6,254,632 B1 | 7/2001 | Wu et al. |
| 6,273,908 B1 | 8/2001 | Ndondo-Lay |
| 6,273,913 B1 | 8/2001 | Wright et al. |
| 6,280,411 B1 | 8/2001 | Lennox |
| 6,290,673 B1 | 9/2001 | Shanley |
| 6,293,967 B1 | 9/2001 | Shanley |
| 6,299,604 B1 | 10/2001 | Ragheb et al. |
| 6,306,166 B1 | 10/2001 | Barry et al. |
| 6,309,414 B1 | 10/2001 | Rolando et al. |
| 6,358,556 B1 | 3/2002 | Ding et al. |
| 6,358,989 B1 | 3/2002 | Kunz et al. |
| 6,379,381 B1 * | 4/2002 | Hossainy et al. ............ 623/1.42 |
| 6,399,144 B2 | 6/2002 | Dinh et al. |
| 6,403,635 B1 | 6/2002 | Kinsella et al. |
| 6,423,092 B2 | 7/2002 | Datta et al. |
| 6,429,232 B1 | 8/2002 | Kinsella et al. |
| 6,491,666 B1 | 12/2002 | Santini et al. |
| 6,491,938 B2 | 12/2002 | Kunz et al. |
| 6,497,916 B1 | 12/2002 | Taylor et al. |
| 6,500,859 B2 | 12/2002 | Kinsella et al. |
| 6,506,437 B1 * | 1/2003 | Harish et al. ................. 427/2.25 |
| 6,515,009 B1 | 2/2003 | Kunz et al. |
| 6,537,256 B2 | 3/2003 | Santini et al. |
| 6,551,838 B2 | 4/2003 | Santini et al. |
| 6,558,733 B1 | 5/2003 | Hossainy et al. |
| 6,562,065 B1 | 5/2003 | Shanley |
| 6,565,602 B2 | 5/2003 | Rolando et al. |
| 6,569,441 B2 | 5/2003 | Kunz et al. |
| 6,569,688 B2 | 5/2003 | Sivan et al. |
| 6,585,764 B2 | 7/2003 | Wright et al. |
| 6,599,928 B2 | 7/2003 | Kunz et al. |
| 6,613,084 B2 | 9/2003 | Yang |
| 6,645,547 B1 | 11/2003 | Shekalim et al. |
| 6,656,162 B2 | 12/2003 | Santini et al. |
| 6,663,881 B2 | 12/2003 | Kunz et al. |
| 6,673,385 B1 | 1/2004 | Ding et al. |
| 6,682,545 B1 | 1/2004 | Kester |
| 6,702,850 B1 | 3/2004 | Byun et al. |
| 6,706,061 B1 | 3/2004 | Fischell et al. |
| 6,712,845 B2 | 3/2004 | Hossainy |
| 6,713,119 B2 | 3/2004 | Hossainy et al. |
| 6,716,444 B1 | 4/2004 | Castro et al. |
| 6,720,350 B2 | 4/2004 | Kunz et al. |
| 6,723,373 B1 | 4/2004 | Narayanan et al. |
| 6,730,064 B2 | 5/2004 | Ragheb et al. |
| 6,730,116 B1 | 5/2004 | Wolinsky et al. |
| 6,758,859 B1 | 7/2004 | Dang et al. |
| 6,783,543 B2 | 8/2004 | Jang |
| 2001/0018469 A1 | 8/2001 | Chen et al. |
| 2001/0027340 A1 | 10/2001 | Wright et al. |
| 2001/0029351 A1 | 10/2001 | Falotico et al. |
| 2001/0034363 A1 | 10/2001 | Li et al. |
| 2001/0044652 A1 | 11/2001 | Moore |
| 2002/0002400 A1 | 1/2002 | Drasler et al. |
| 2002/0005206 A1 | 1/2002 | Falotico et al. |
| 2002/0007209 A1 | 1/2002 | Scheerder et al. |
| 2002/0007213 A1 | 1/2002 | Falotico et al. |
| 2002/0016625 A1 | 2/2002 | Falotico et al. |
| 2002/0019661 A1 | 2/2002 | Datta et al. |
| 2002/0022876 A1 | 2/2002 | Richter et al. |
| 2002/0032414 A1 | 3/2002 | Ragheb et al. |
| 2002/0038145 A1 | 3/2002 | Jang |
| 2002/0068969 A1 | 6/2002 | Shanley et al. |
| 2002/0071902 A1 | 6/2002 | Ding et al. |
| 2002/0072511 A1 | 6/2002 | New et al. |
| 2002/0082680 A1 | 6/2002 | Shanley et al. |
| 2002/0082682 A1 | 6/2002 | Barclay et al. |
| 2002/0094985 A1 | 7/2002 | Herrmann et al. |
| 2002/0142039 A1 | 10/2002 | Claude |
| 2002/0155212 A1 | 10/2002 | Hossainy |
| 2002/0183581 A1 * | 12/2002 | Yoe et al. ..................... 600/3 |
| 2002/0193475 A1 | 12/2002 | Hossainy et al. |
| 2003/0028243 A1 | 2/2003 | Bates et al. |
| 2003/0028244 A1 | 2/2003 | Bates et al. |
| 2003/0036794 A1 | 2/2003 | Ragheb et al. |
| 2003/0050687 A1 | 3/2003 | Schwade et al. |
| 2003/0060877 A1 | 3/2003 | Falotico et al. |
| 2003/0068355 A1 | 4/2003 | Shanley et al. |
| 2003/0077312 A1 | 4/2003 | Schmulewicz et al. |
| 2003/0083646 A1 | 5/2003 | Sirhan et al. |
| 2003/0086957 A1 | 5/2003 | Hughes et al. |
| 2003/0088307 A1 | 5/2003 | Shulze et al. |
| 2003/0100865 A1 | 5/2003 | Santini et al. |
| 2003/0125803 A1 | 7/2003 | Vallana et al. |
| 2003/0157241 A1 | 8/2003 | Hossainy et al. |
| 2003/0176915 A1 | 9/2003 | Wright et al. |
| 2003/0181973 A1 | 9/2003 | Sahota |
| 2003/0199970 A1 | 10/2003 | Shanley |
| 2003/0204239 A1 | 10/2003 | Carlyle et al. |
| 2003/0216699 A1 | 11/2003 | Falotico |
| 2004/0010306 A1 | 1/2004 | Freyman et al. |
| 2004/0073296 A1 | 4/2004 | Epstein et al. |
| 2004/0122505 A1 | 6/2004 | Shanley |
| 2004/0122506 A1 | 6/2004 | Shanley et al. |
| 2004/0127976 A1 | 7/2004 | Diaz |
| 2004/0127977 A1 | 7/2004 | Shanley |

FOREIGN PATENT DOCUMENTS

| | | |
|---|---|---|
| CA | 2409787 A1 | 12/2001 |
| EP | 0 470 569 B1 | 2/1992 |
| EP | 0335341 A1 | 3/1992 |
| EP | 0 556 245 B1 | 1/1993 |
| EP | 0 540 290 B1 | 5/1993 |
| EP | 0 567 816 A1 | 11/1993 |
| EP | 0 734 698 B1 | 10/1996 |
| EP | 0 706 376 B1 | 4/1997 |
| EP | 0 850 604 B1 | 7/1998 |
| EP | 0 850 651 B1 | 7/1998 |
| EP | 0 875 218 B1 | 11/1998 |
| EP | 0 887 051 B1 | 12/1998 |
| EP | 0 897 700 B1 | 2/1999 |
| EP | 1 132 058 A1 | 9/2001 |
| EP | 1 172 074 A2 | 1/2002 |
| EP | 1 181 943 A1 | 2/2002 |
| EP | 1 222 941 B1 | 7/2002 |
| EP | 1 223 305 B1 | 7/2002 |
| EP | 1 236 478 B1 | 9/2002 |
| EP | 0747069 A2 | 9/2002 |
| EP | 1348402 A1 | 10/2003 |
| EP | 0950386 A2 | 4/2004 |
| EP | 0824902 A1 | 11/2004 |
| EP | 1277449 B1 | 6/2006 |
| EP | 1 772 114 A1 | 4/2007 |
| FR | 2 683 449 A1 | 5/1993 |
| FR | 2 764 794 A1 | 12/1998 |
| GB | 20200220 U1 | 4/2002 |
| JP | 9099056 A | 4/1997 |
| JP | 2004500153 A | 1/2004 |
| WO | WO 90/01969 A1 | 3/1990 |
| WO | WO 90/13332 A1 | 11/1990 |
| WO | WO 91/10424 A1 | 7/1991 |
| WO | WO 91/11193 A1 | 8/1991 |
| WO | WO 91/12779 A1 | 9/1991 |
| WO | WO 91/17789 A1 | 11/1991 |
| WO | WO 92/00747 A1 | 1/1992 |
| WO | WO 92/12717 A2 | 8/1992 |
| WO | WO 92/15286 A1 | 9/1992 |
| WO | WO 93/06792 A1 | 4/1993 |
| WO | WO 93/11120 A1 | 6/1993 |
| WO | WO 94/07529 A1 | 4/1994 |
| WO | WO 94/21308 A1 | 9/1994 |
| WO | WO 94/24961 A1 | 11/1994 |
| WO | WO 94/24962 A1 | 11/1994 |
| WO | WO 95/03036 A1 | 2/1995 |
| WO | WO 95/03795 A1 | 2/1995 |
| WO | WO 95/03796 A1 | 2/1995 |
| WO | WO 95/24908 A1 | 9/1995 |
| WO | WO 95/34255 A1 | 12/1995 |
| WO | WO 96/03092 A1 | 2/1996 |
| WO | WO 96/25176 A1 | 8/1996 |
| WO | WO 96/29028 A1 | 9/1996 |
| WO | WO 97/04721 A1 | 2/1997 |
| WO | WO 97/10011 A1 | 3/1997 |
| WO | WO 97/40783 A2 | 11/1997 |
| WO | WO 98/06092 A1 | 2/1998 |
| WO | WO 98/08566 A1 | 3/1998 |
| WO | WO 98/19628 A1 | 5/1998 |
| WO | WO 98/23244 A1 | 6/1998 |

| | | | |
|---|---|---|---|
| WO | WO 98/36784 A1 | 8/1998 |
| WO | WO 98/58600 A1 | 12/1998 |
| WO | WO 99/15108 A2 | 4/1999 |
| WO | WO 99/16477 A2 | 4/1999 |
| WO | WO 99/36002 A1 | 7/1999 |
| WO | WO 99/39661 A1 | 8/1999 |
| WO | WO 99/44536 A1 | 9/1999 |
| WO | WO 99/49810 A1 | 10/1999 |
| WO | WO 99/49928 A1 | 10/1999 |
| WO | WO 99/55395 A1 | 11/1999 |
| WO | WO 99/55396 A1 | 11/1999 |
| WO | WO 00/10613 A2 | 3/2000 |
| WO | WO 00/10622 A1 | 3/2000 |
| WO | WO 00/40278 A1 | 7/2000 |
| WO | WO 00/69368 A2 | 11/2000 |
| WO | WO 00/71054 A1 | 11/2000 |
| WO | WO 01/17577 A1 | 3/2001 |
| WO | WO 01/45862 A1 | 6/2001 |
| WO | WO 01/49338 A1 | 7/2001 |
| WO | WO 01/52915 A1 | 7/2001 |
| WO | WO 01/87376 A1 | 11/2001 |
| WO | WO 01/93781 A2 | 12/2001 |
| WO | WO 02/17880 A2 | 3/2002 |
| WO | 02/32347 A2 | 4/2002 |
| WO | WO 02/26162 A2 | 4/2002 |
| WO | WO 02/26281 A1 | 4/2002 |
| WO | WO 02/060506 A1 | 8/2002 |
| WO | WO 02/087586 A1 | 11/2002 |
| WO | WO02089706 A1 | 11/2002 |
| WO | WO 03/007842 A2 | 1/2003 |
| WO | 03/009779 A2 | 2/2003 |
| WO | WO03015664 A1 | 2/2003 |
| WO | WO 03/047463 A1 | 6/2003 |
| WO | WO 2004/043511 A1 | 5/2004 |

OTHER PUBLICATIONS

European Search Report dated Nov. 12, 2010 in appl'n EP10011318.
European Search Report dated Nov. 12, 2010 in appl'n EP10011317.
European Search Report dated Dec. 8, 2010 in appl'n EP10010945.
European Search Report dated Dec. 8, 2010 in appl'n EP10010946.
European Search Report dated Dec. 8, 2010 in appl'n EP10010947.
Australian Office Action dated May 3, 2010 corresponding to Application No. 2005251777.
European Office Action dated Jun. 11, 2010 in Application No. 09009102.6.
Japanese Office Action dated Aug. 24, 2010 in Application No. 2007-527604.

* cited by examiner

EXPANDABLE MEDICAL DEVICE WITH
BENEFICIAL AGENT CONCENTRATION
GRADIENT

This application is a continuation of, and claims priority under 35 U.S.C. §120 to, U.S. application Ser. No. 10/857,201, filed 27 May 2004 (now abandoned), which is a continuation-in-part of U.S. application Ser. No. 10/668,430, filed Sep. 22, 2003, which claims priority to U.S. Provisional Application No. 60/412,489, filed Sep. 20, 2002. U.S. application Ser. No. 10/857,201 is also a continuation-in-part of U.S. application Ser. No. 10/253,020, filed on Sep. 23, 2002, now U.S. Pat. No. 7,208,011, which is a continuation-in-part of U.S. application Ser. No. 09/948,989, filed on Sep. 7, 2001, now U.S. Pat. No. 7,208,010, which claims priority to U.S. Provisional Application No. 60/314,259, filed Aug. 20, 2001, and which is a continuation-in-part of U.S. application Ser. No. 09/688,092, filed Oct. 16, 2000 (now abandoned), which is a continuation-in-part of U.S. application Ser. No. 09/183,555, filed Oct. 29, 1998, now U.S. Pat. No. 6,241,762, which claims priority to U.S. Provisional Application No. 60/079,881, filed Mar. 30, 1998. The entirety of each of these documents is incorporated by reference herein.

FIELD OF THE INVENTION

The present invention relates to tissue-supporting medical devices, and more particularly to expandable, non-removable devices that are implanted within a bodily lumen of a living animal or human to support the organ and maintain patency, and that can deliver a beneficial agent to the intervention site.

BACKGROUND OF THE INVENTION

In the past, permanent or biodegradable devices have been developed for implantation within a body passageway to maintain patency of the passageway. These devices are typically introduced percutaneously, and transported transluminally until positioned at a desired location. These devices are then expanded either mechanically, such as by the expansion of a mandrel or balloon positioned inside the device, or expand themselves by releasing stored energy upon actuation within the body. Once expanded within the lumen, these devices, called stents, become encapsulated within the body tissue and remain a permanent implant.

U.S. Pat. No. 6,241,762, which is incorporated herein by reference in its entirety, discloses a non-prismatic stent design which remedies the above mentioned performance deficiencies of previous stents. In addition, preferred embodiments of this patent provide a stent with large, non-deforming strut and link elements, which can contain holes without compromising the mechanical properties of the strut or link elements, or the device as a whole. Further, these holes may serve as large, protected reservoirs for delivering various beneficial agents to the device implantation site.

Of the many problems that may be addressed through stent-based local delivery of beneficial agents, one of the most important is restenosis. Restenosis is a major complication that can arise following vascular interventions such as angioplasty and the implantation of stents. Simply defined, restenosis is a wound healing process that reduces the vessel lumen diameter by extracellular matrix deposition and vascular smooth muscle cell proliferation, and which may ultimately result in renarrowing or even reocclusion of the lumen. Despite the introduction of improved surgical techniques, devices and pharmaceutical agents, the overall restenosis rate is still reported in the range of 25% to 50% within six to twelve months after an angioplasty procedure. To treat this condition, additional revascularization procedures are frequently required, thereby increasing trauma and risk to the patient.

SUMMARY

According to a first aspect of the invention, a method of forming an implantable medical device configured to release at least one therapeutic agent therefrom, wherein the therapeutic agent is disposed in a matrix affixed to the body of the implantable medical device, the body includes at least one recess, and wherein the concentration of the at least one therapeutic agent in the matrix varies as a continuous gradient relative to a surface of the body of the implantable medical device, comprises forming a first homogeneous solution comprising the at least one therapeutic agent mixed with a polymeric binder, applying introducing the first homogeneous solution into the at least one recess in the body of the implantable medical device, solidifying the first homogeneous solution, thereby forming a first portion of the matrix, forming a second homogeneous solution comprising the polymeric binder, applying the second homogeneous solution to the first portion of the matrix, thereby at least partially liquefying the first portion of the matrix, and solidifying the second homogeneous solution, thereby forming a second portion of the matrix, wherein the concentration of the at least one therapeutic agent in the matrix is different in the first and second portions of the matrix.

Still other aspects, features, and attendant advantages of the present invention will become apparent to those skilled in the art from a reading of the following detailed description of embodiments constructed in accordance therewith, taken in conjunction with the accompanying drawings.

BRIEF DESCRIPTION OF THE DRAWINGS

The invention will now be described in greater detail with reference to the preferred embodiments illustrated in the accompanying drawings, in which like elements bear like reference numerals, and wherein.

DETAILED DESCRIPTION OF EXEMPLARY EMBODIMENTS

Figure 1:
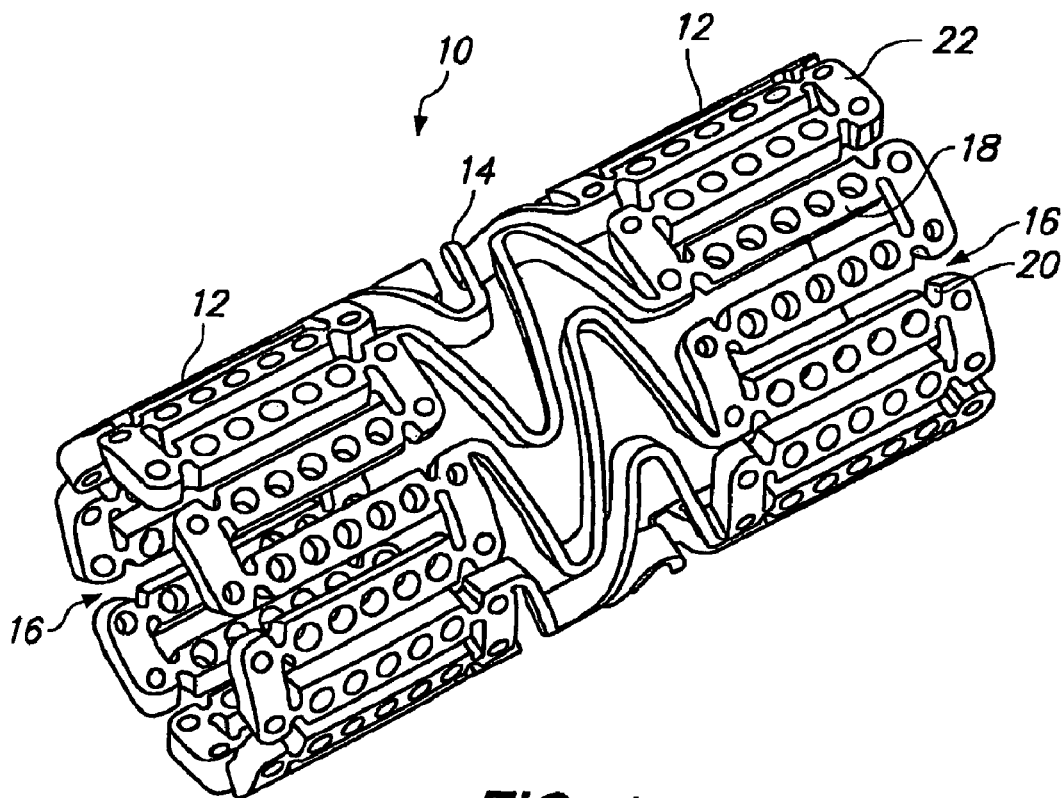
FIG. 1 is a perspective view of a tissue supporting device in accordance with a first preferred embodiment of the present invention.
Figure 2:
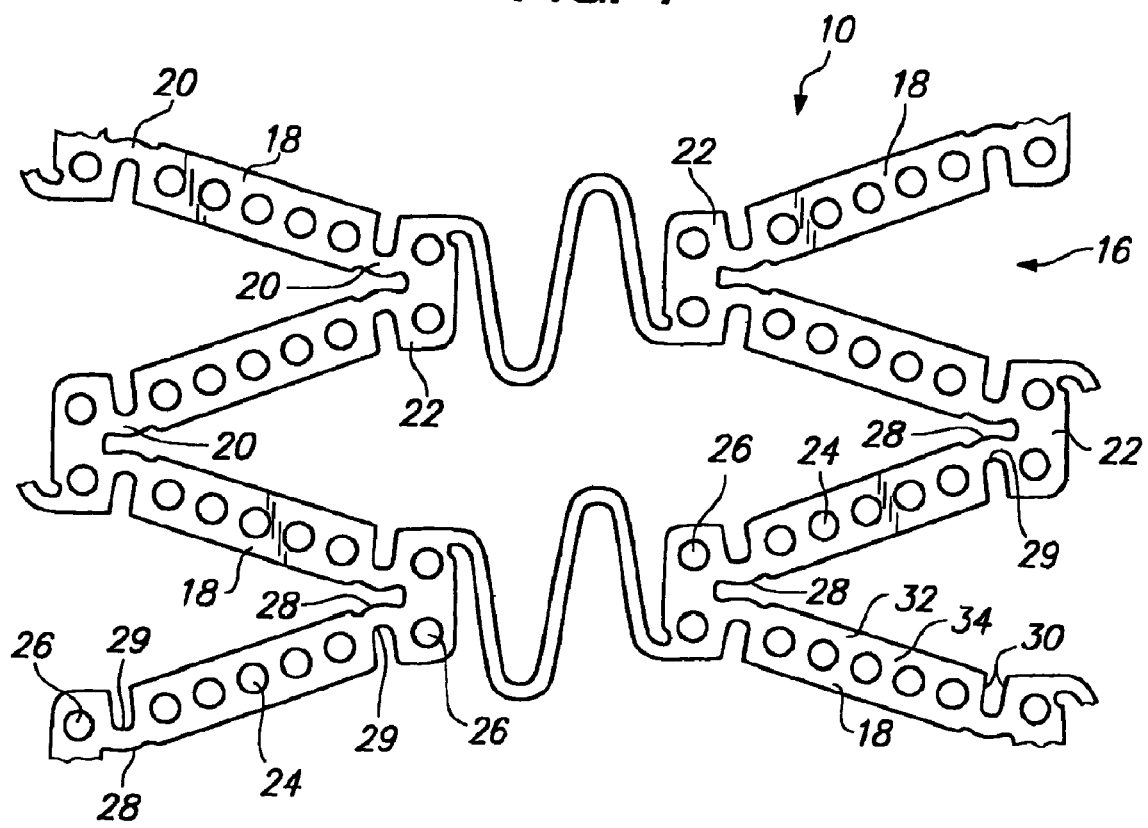
FIG. 2 is an enlarged side view of a portion of the device of FIG. 1.

Referring to FIGS. 1 and 2, a tissue supporting device in accordance with one preferred embodiment of the present invention is shown generally by reference numeral 10. The tissue supporting device 10 includes a plurality of cylindrical tubes 12 connected by S-shaped bridging elements 14. The bridging elements 14 allow the tissue supporting device to bend axially when passing through the tortuous path of the vasculature to the deployment site and allow the device to bend when necessary to match the curvature of a vessel wall to be supported. Each of the cylindrical tubes 12 has a plurality of axial slots 16 extending from an end surface of the cylindrical tube toward an opposite end surface.

Formed between the slots 16 is a network of axial struts 18 and links 22. The struts 18 and links 22 are provided with openings for receiving and delivering a beneficial agent. As will be described below with respect to FIGS. 9-17, the beneficial agent is loaded into the openings in layers or other configurations which provide control over the temporal release kinetics of the agent.

Each individual strut 18 is preferably linked to the rest of the structure through a pair of reduced sections 20, one at each end, which act as stress/strain concentration features. The reduced sections 20 of the struts function as hinges in the cylindrical structure. Since the stress/strain concentration features are designed to operate into the plastic deformation range of generally ductile materials, they are referred to as ductile hinges 20. The ductile hinges 20 are described in further detail in U.S. Pat. No. 6,241,762, which is incorporated herein by reference.

With reference to the drawings and the discussion, the width of any feature is defined as its dimension in the circumferential direction of the cylinder. The length of any feature is defined as its dimension in the axial direction of the cylinder. The thickness of any feature is defined as the wall thickness of the cylinder.

The presence of the ductile hinges 20 allows all of the remaining features in the tissue supporting device to be increased in width or the circumferentially oriented component of their respective rectangular moments of inertia—thus greatly increasing the strength and rigidity of these features. The net result is that elastic, and then plastic, deformation commences and propagate in the ductile hinges 20 before other structural elements of the device undergo any significant elastic deformation. The force required to expand the tissue supporting device 10 becomes a function of the geometry of the ductile hinges 20, rather than the device structure as a whole, and arbitrarily small expansion forces can be specified by changing hinge geometry for virtually any material wall thickness. The ability to increase the width and thickness of the struts 18 and links 22 provides additional area and depth for the beneficial agent receiving openings.

In the embodiment of FIGS. 1 and 2, it is desirable to increase the width of the individual struts 18 between the ductile hinges 20 to the maximum width that is geometrically possible for a given diameter and a given number of struts arrayed around that diameter. The only geometric limitation on strut width is the minimum practical width of the slots 16 which is about 0.002 inches (0.0508 mm) for laser machining. Lateral stiffness of the struts 18 increases as the cube of strut width, so that relatively small increases in strut width significantly increase strut stiffness. The net result of inserting ductile hinges 20 and increasing strut width is that the struts 18 no longer act as flexible leaf springs, but act as essentially rigid beams between the ductile hinges. All radial expansion or compression of the cylindrical tissue supporting device 10 is accommodated by mechanical strain in the hinge features 20, and yield in the hinge commences at very small overall radial expansion or compression.

The ductile hinge 20 illustrated in FIGS. 1 and 2 is exemplary of a preferred structure that will function as a stress/strain concentrator. Many other stress/strain concentrator configurations may also be used as the ductile hinges in the present invention, as shown and described by way of example in U.S. Pat. No. 6,241,762. The geometric details of the stress/strain concentration features or ductile hinges 20 can be varied greatly to tailor the exact mechanical expansion properties to those required in a specific application.

Although a tissue supporting device configuration has been illustrated in FIG. 1 which includes ductile hinges, it should be understood that the beneficial agent may be contained in openings in stents having a variety of designs including the designs illustrated in U.S. Provisional Patent Application Ser. No. 60/314,360, filed on Aug. 20, 2001 and U.S. patent application Ser. No. 09/948,987, filed on Sep. 7, 2001, which are incorporated herein by reference. The present invention incorporating beneficial agent openings may also be used with other known stent designs.

As shown in FIGS. 1-4, at least one and more preferably a series of openings 24 are formed by laser drilling or any other means known to one skilled in the art at intervals along the neutral axis of the struts 18. Similarly, at least one and preferably a series of openings 26 are formed at selected locations in the links 22. Although the use of openings 24 and 26 in both the struts 18 and links 22 is preferred, it should be clear to one skilled in the art that openings could be formed in only one of the struts and links. Openings may also be formed in the bridging elements 14. In the embodiment of FIGS. 1 and 2, the openings 24, 26 are circular in nature and form cylindrical holes extending through the width of the tissue supporting device 10. It should be apparent to one skilled in the art, however, that openings of any geometrical shape or configuration could of course be used without departing from the scope of the present invention. In addition, openings having a depth less than the thickness of the device may also be used.

The behavior of the struts 18 in bending is analogous to the behavior of an I-beam or truss. The outer edge elements 32 of the struts 18, shown in FIG. 2, correspond to the I-beam flange and carry the tensile and compressive stresses, whereas the inner elements 34 of the struts 18 correspond to the web of an I-beam which carries the shear and helps to prevent buckling and wrinkling of the faces. Since most of the bending load is carried by the outer edge elements 32 of the struts 18, a concentration of as much material as possible away from the neutral axis results in the most efficient sections for resisting strut flexure. As a result, material can be judiciously removed along the axis of the strut so as to form openings 24, 26 without adversely impacting the strength and rigidity of the strut. Since the struts 18 and links 22 thus formed remain essentially rigid during stent expansion, the openings 24, 26 are also non-deforming.

The openings 24, 26 in the struts 18 may promote the healing of the intervention site by promoting regrowth of the endothelial cells. By providing the openings 24, 26 in the struts, 18, the cross section of the strut is effectively reduced without decreasing the strength and integrity of the strut, as described above. As a result, the overall distance across which endothelial cell regrowth must occur is also reduced to approximately 0.0025-0.0035 inches, which is approximately one-half of the thickness of a conventional stent. It is further believed that during insertion of the expandable medical device, cells from the endothelial layer may be scraped from the inner wall of the vessel by the openings 24, 26 and remain therein after implantation. The presence of such endothelial cells would thus provide a basis for the healing of the vessel wall.

The openings 24, 26 are loaded with an agent, most preferably a beneficial agent, for delivery to the vessel wall which the tissue supporting device 10 is supporting. The terms "agent" and "beneficial agent" as used herein are intended to have their broadest possible interpretation and are used to include any therapeutic agent or drug, as well as inactive agents such as barrier layers or carrier layers. The terms "drug" and "therapeutic agent" are used interchangeably to refer to any therapeutically active substance that is delivered to a bodily conduit of a living being to produce a desired, usually beneficial, effect. The present invention is particularly well suited for the delivery of antiproliferatives (anti-restenosis agents) such as paclitaxel and rapamycin for example, and antithrombins such as heparin, for example.

Additional uses, however, include therapeutic agents in all the major therapeutic areas including, but not limited to: anti-infectives such as antibiotics and antiviral agents; analgesics, including fentanyl, sufentanil, buprenorphine and analgesic combinations; anesthetics; anorexics; antiarthritics; antiasthmatic agents such as terbutaline; anticonvulsants; antidepressants; antidiabetic agents; antidiarrheals; antihistamines; anti-inflammatory agents; antimigraine preparations; antimotion sickness preparations such as scopolamine and ondansetron; antinauseants; antineoplastics; antiparkinsonism drugs; antipruritics; antipsychotics; antipyretics; antispasmodics, including gastrointestinal and urinary; anticholinergics; sympathomimetrics; xanthine derivatives; cardiovascular preparations, including calcium channel blockers such as nifedipine; beta blockers; beta-agonists such as dobutamine and ritodrine; antiarrythmics; antihypertensives such as atenolol; ACE inhibitors such as ranitidine; diuretics; vasodilators, including general, coronary, peripheral, and cerebral; central nervous system stimulants; cough and cold preparations; decongestants; diagnostics; hormones such as parathyroid hormone; hypnotics; immunosuppressants; muscle relaxants; parasympatholytics; parasympathomimetrics; prostaglandins; proteins; peptides; psychostimulants; sedatives; and tranquilizers.

The beneficial agents used in the present invention include classical small molecular weight therapeutic agents commonly referred to as drugs including all classes of action as exemplified by, but not limited to: antiproliferatives, antithrombins, antiplatelet, antilipid, anti-inflammatory, angiogenic, anti-angiogenic, vitamins, ACE inhibitors, vasoactive substances, antimitotics, metello-proteinase inhibitors, NO donors, estradiols, anti-sclerosing agents, alone or in combination. Beneficial agent also includes larger molecular weight substances with drug like effects on target tissue sometimes called biologic agents including but not limited to: peptides, lipids, protein drugs, enzymes, oligonucleotides, ribozymes, genetic material, prions, virus, bacteria, and eukaryotic cells such as endothelial cells, monocyte/macrophages or vascular smooth muscle cells to name but a few examples. The therapeutic agent may also be a pro-drug, which metabolizes into the desired drug when administered to a host. Other beneficial agents may include but not be limited to physical agents such as microcapsules, microspheres, microbubbles, liposomes, niosomes, radioactive isotopes, emulsions, dispersions, or agents activated by some other form of energy such as light or ultrasonic energy, or by other circulating molecules that can be systemically administered.

The embodiment of the invention shown in FIGS. 1 and 2 can be further refined by using Finite Element Analysis and other techniques to optimize the deployment of the beneficial agent within the openings of the struts and links. Basically, the shape and location of the openings 24, 26 can be modified to maximize the volume of the voids while preserving the relatively high strength and rigidity of the struts 18 with respect to the ductile hinges 20.

Figure 3:
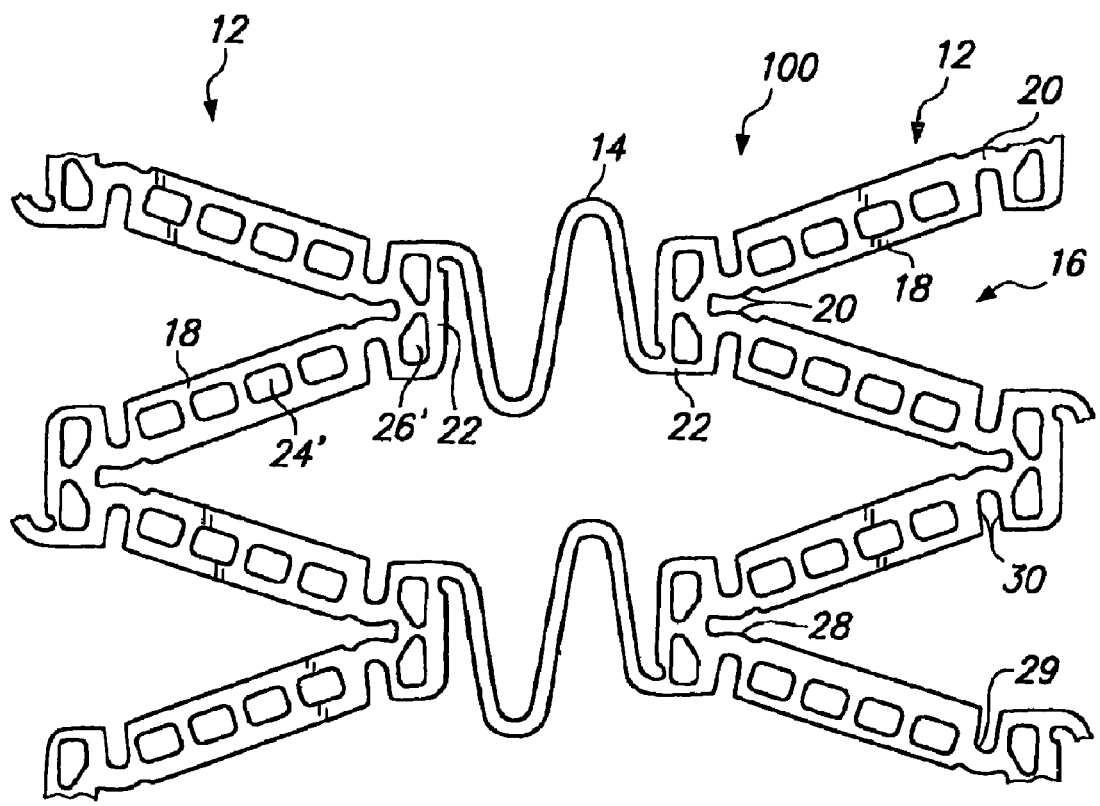
FIG. 3 is an enlarged side view of a tissue supporting device in accordance with a further preferred embodiment of the present invention.

FIG. 3 illustrates a further preferred embodiment of the present invention, wherein like reference numerals have been used to indicate like components. The tissue supporting device 100 includes a plurality of cylindrical tubes 12 connected by S-shaped bridging elements 14. Each of the cylindrical tubes 12 has a plurality of axial slots 16 extending from an end surface of the cylindrical tube toward an opposite end surface. Formed between the slots 16 is a network of axial struts 18 and links 22. Each individual strut 18 is linked to the rest of the structure through a pair of ductile hinges 20, one at each end, which act as stress/strain concentration features. Each of the ductile hinges 20 is formed between an arc surface 28 and a concave notch surface 29.

At intervals along the neutral axis of the struts 18, at least one and more preferably a series of openings 24' are formed by laser drilling or any other means known to one skilled in the art. Similarly, at least one and preferably a series of openings 26' are formed at selected locations in the links 22. Although the use of openings 24', 26' in both the struts 18 and links 22 is preferred, it should be clear to one skilled in the art that openings could be formed in only one of the struts and links. In the illustrated embodiment, the openings 24' in the struts 18 are generally rectangular whereas the openings 26' in the links 22 are polygonal. It should be apparent to one skilled in the art, however, that openings of any geometrical shape or configuration could of course be used, and that the shape of openings 24, 24' may be the same or different from the shape of openings 26, 26', without departing from the scope of the present invention. As described in detail above, the openings 24', 26' may be loaded with an agent, most preferably a beneficial agent, for delivery to the vessel in which the tissue support device 100 is deployed. Although the openings 24', 26' are preferably through openings, they may also be recesses extending only partially through the thickness of the struts and links.

The relatively large, protected openings 24, 24', 26, 26', as described above, make the expandable medical device of the present invention particularly suitable for delivering agents having more esoteric larger molecules or genetic or cellular agents, such as, for example, protein drugs, enzymes, antibodies, antisense oligonucleotides, ribozymes, gene/vector constructs, and cells (including but not limited to cultures of a patient's own endothelial cells). Many of these types of agents are biodegradable or fragile, have a very short or no shelf life, must be prepared at the time of use, or cannot be pre-loaded into delivery devices such as stents during the manufacture thereof for some other reason. The large through openings in the expandable device of the present invention form protected areas or receptors to facilitate the loading of such an agent either at the time of use or prior to use, and to protect the agent from abrasion and extrusion during delivery and implantation.

The volume of beneficial agent that can be delivered using through openings is about 3 to 10 times greater than the volume of a 5 micron coating covering a stent with the same stent/vessel wall coverage ratio. This much larger beneficial agent capacity provides several advantages. The larger capacity can be used to deliver multi-drug combinations, each with independent release profiles, for improved efficacy. Also, larger capacity can be used to provide larger quantities of less aggressive drugs and to achieve clinical efficacy without the undesirable side-effects of more potent drugs, such as retarded healing of the endothelial layer.

Through openings also decrease the surface area of the beneficial agent bearing compounds to which the vessel wall surface is exposed. For typical devices with beneficial agent openings, this exposure decreases by a factors ranging from about 6:1 to 8:1, by comparison with surface coated stents. This dramatically reduces the exposure of vessel wall tissue to polymer carriers and other agents that can cause inflammation, while simultaneously increasing the quantity of beneficial agent delivered, and improving control of release kinetics.

Figure 4:
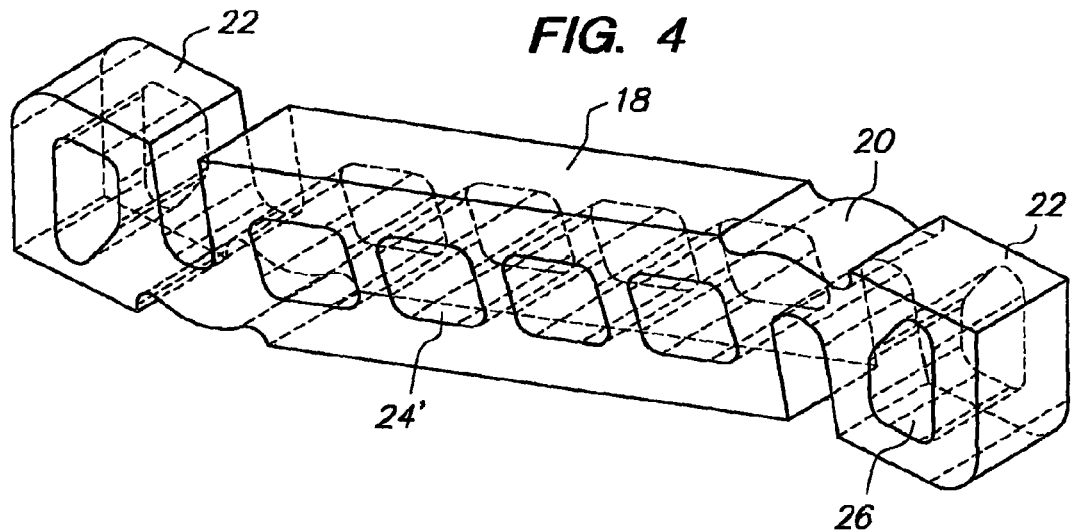
FIG. 4 is an enlarged side view of a portion of the stent shown in FIG. 3.
Figure 5:
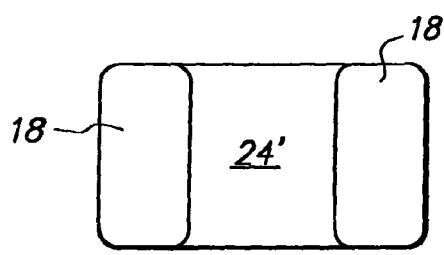
FIG. 5 is an enlarged cross section of an opening.
Figure 6:
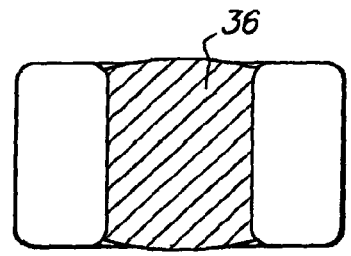
FIG. 6 is an enlarged cross section of an opening illustrating beneficial agent loaded into the opening.
Figure 7:
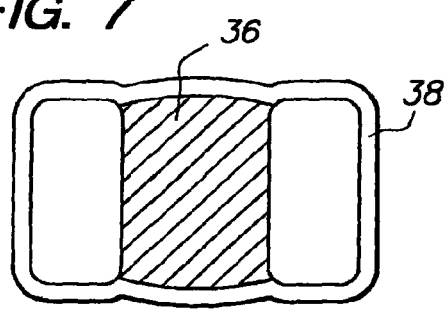
FIG. 7 is an enlarged cross section of an opening illustrating a beneficial agent loaded into the opening and a thin coating of a beneficial agent.
Figure 8:
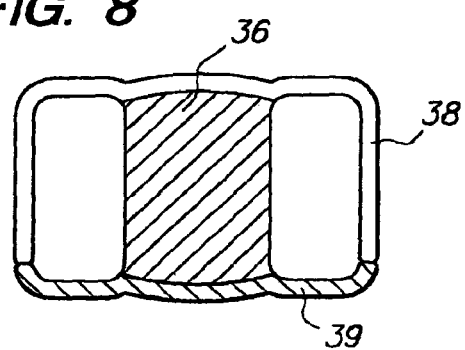
FIG. 8 is an enlarged cross section of an opening illustrating a beneficial agent loaded into the opening and thin coatings of different beneficial agents on different surfaces of the device.

FIG. 4 shows an enlarged view of one of the struts 18 of device 100 disposed between a pair of ductile hinges 20 having a plurality of openings 24'. FIG. 5 illustrates a cross section of one of the openings 24' shown in FIG. 4. FIG. 6 illustrates the same cross section when a beneficial agent 36 has been loaded into the opening 24' of the strut 18. Optionally, after loading the opening 24' and/or the opening 26' with a beneficial agent 36, the entire exterior surface of the stent can be coated with a thin layer of a beneficial agent 38, which may be the same as or different from the beneficial agent 36, as schematically shown in FIG. 7. Still further, another variation of the present invention would coat the outwardly facing surfaces of the stent with a first beneficial agent 38 while coating the inwardly facing surfaces of the stent with a different beneficial agent 39, as illustrated in FIG. 8. The inwardly facing surface of the stent would be defined as at least the surface of the stent which, after expansion, forms the inner passage of the vessel. The outwardly facing surface of the stent would be defined as at least the surface of the stent which, after expansion, is in contact with and directly supports the inner wall of the vessel. The beneficial agent 39 coated on the inner surfaces may be a barrier layer which prevents the beneficial agent 36 from passing into the lumen of the blood vessel and being washed away in the blood stream.

Figure 9:
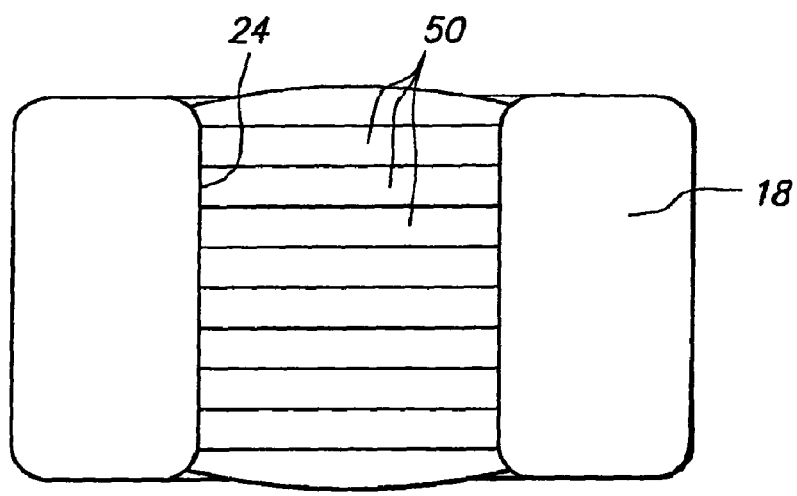
FIG. 9 is an enlarged cross section of an opening illustrating a beneficial agent provided in a plurality of layers.

FIG. 9 shows a cross section of an opening 24 in which one or more beneficial agents have been loaded into the opening 24 in discrete layers 50. One method of creating such layers is to deliver a solution comprising beneficial agent, polymer carrier, and a solvent into the opening and evaporating the solvent to create a thin solid layer of beneficial agent in the carrier. Other methods of delivering the beneficial agent can also be used to create layers. According to another method for creating layers, a beneficial agent may be loaded into the openings alone if the agent is structurally viable without the need for a carrier. The process can then be repeated until each opening is partially or entirely filled.

In a typical embodiment, the total depth of the opening 24 is about 125 to about 140 microns, and the typical layer thickness would be about 2 to about 50 microns, preferably about 12 microns. Each typical layer is thus individually about twice as thick as the typical coating applied to surface-coated stents. There would be at least two and preferably about ten to twelve such layers in a typical opening, with a total beneficial agent thickness about 25 to 28 times greater than a typical surface coating. According to one preferred embodiment of the present invention, the openings have an area of at least 5.times. 10.sup.−6 square inches, and preferably at least 7.times. 10. sup.−6 square inches.

Since each layer is created independently, individual chemical compositions and pharmacokinetic properties can be imparted to each layer. Numerous useful arrangements of such layers can be formed, some of which will be described below. Each of the layers may include one or more agents in the same or different proportions from layer to layer. The layers may be solid, porous, or filled with other drugs or excipients.

FIG. 9 shows the simplest arrangement of layers including identical layers 50 that together form a uniform, homogeneous distribution of beneficial agent. If the carrier polymer were comprised of a biodegradable material, then erosion of the beneficial agent containing carrier would occur on both faces of the opening at the same time, and beneficial agent would be released at an approximately linear rate over time corresponding to the erosion rate of the carrier. This linear or constant release rate is referred to as a zero order delivery profile. Use of biodegradable carriers in combination with through openings is especially useful, to guarantee 100% discharge of the beneficial agent within a desired time without creating virtual spaces or voids between the radially outer-most surface of the stent and tissue of the vessel wall. When the biodegradable material in the through openings is removed, the openings may provide a communication between the strut-covered vessel wall and the blood stream. Such communication may accelerate vessel healing and allow the ingrowth of cells and extracellular components that more thoroughly lock the stent in contact with the vessel wall. Alternatively, some through-openings may be loaded with beneficial agent while others are left unloaded. The unloaded holes could provide an immediate nidus for the ingrowth of cells and extracellular components to lock the stent into place, while loaded openings dispense the beneficial agent.

The advantage of complete erosion using the through openings over surface coated stents opens up new possibilities for stent-based therapies. In the treatment of cardiac arrhythmias, such as atrial fibrillation both sustained and paroxysmal, sustained ventricular tachycardia, super ventricular tachycardia including reentrant and ectopic, and sinus tachycardia, a number of techniques under development attempt to ablate tissue in the pulmonary veins or some other critical location using various energy sources, e.g. microwaves, generally referred to as radio-frequency ablation, to create a barrier to the propagation of undesired electrical signals in the form of scar tissue. These techniques have proven difficult to control accurately. A stent based therapy using through openings, biodegradable carriers, and associated techniques described herein could be used to deliver a chemically ablative agent in a specific, precise pattern to a specific area for treatment of atrial fibrillation, while guaranteeing that none of the inherently cytotoxic ablating agent could be permanently trapped in contact with the tissue of the vessel wall.

If, on the other hand, the goal of a particular therapy is to provide a long term effect, beneficial agents located in openings provide an equally dramatic advantage over surface coated devices. In this case, a composition comprising a beneficial agent and a non-biodegradable carrier would be loaded into the through openings, preferably in combination with a diffusion barrier layer as described below. To continue the cardiac arrhythmias example, it might be desirable to introduce a long-term anti-arrhythmic drug near the ostia of the pulmonary veins or some other critical location. The transient diffusion behavior of a beneficial agent through a non-biodegradable carrier matrix can be generally described by Fick's second law:

$$\frac{\partial C_x}{\partial t} = \frac{\partial}{\partial x}\left[D \frac{\partial C_x}{\partial x}\right]$$

Where C is the concentration of beneficial agent at cross section x, x is either the thickness of a surface coating or depth of a through opening, D is the diffusion coefficient and t is time. The solution of this partial differential equation for a through opening with a barrier layer will have the form of a normalized probability integral or Gaussian Error Function, the argument of which will contain the term $$\frac{x}{2\sqrt{Dt}}$$

To compare the time intervals over which a given level of therapy can be sustained for surface coatings vs. through openings, we can use Fick's Second Law to compare the times required to achieve equal concentrations at the most inward surfaces of the coating and opening respectively, i.e. the values of x and t for which the arguments of the Error Function are equal:

$$\frac{x_1}{2\sqrt{Dt_1}} = \frac{x_2}{2\sqrt{Dt_2}} \Rightarrow \frac{x_1^2}{x_2^2} = \frac{t_1}{t_2}$$

The ratio of diffusion times to achieve comparable concentrations thus varies as the square of the ratio of depths. A typical opening depth is about 140 microns while a typical coating thickness is about 5 micron; the square of this ratio is 784, meaning that the effective duration of therapy for through openings is potentially almost three orders of magnitude greater for through openings than for surface coatings of the same composition. The inherent non-linearity of such release profiles can in part be compensated for in the case of through openings, but not in thin surface coatings, by varying the beneficial agent concentration of layers in a through opening as described below. It will be recalled that, in addition to this great advantage in beneficial agent delivery duration, through openings are capable of delivering a 3 to 10 times greater quantity of beneficial agent, providing a decisive overall advantage in sustained therapies. The diffusion example above illustrates the general relationship between depth and diffusion time that is characteristic of a wider class of solid state transport mechanisms.

Beneficial agent that is released to the radially innermost or inwardly facing surface known as the lumen facing surface of an expanded device may be rapidly carried away from the targeted area, for example by the bloodstream, and thus lost. Up to half of the total agent loaded in such situations may have no therapeutic effect due to being carried away by the bloodstream. This is probably the case for all surface coated stents as well as the through opening device of FIG. 9.

Figure 10:
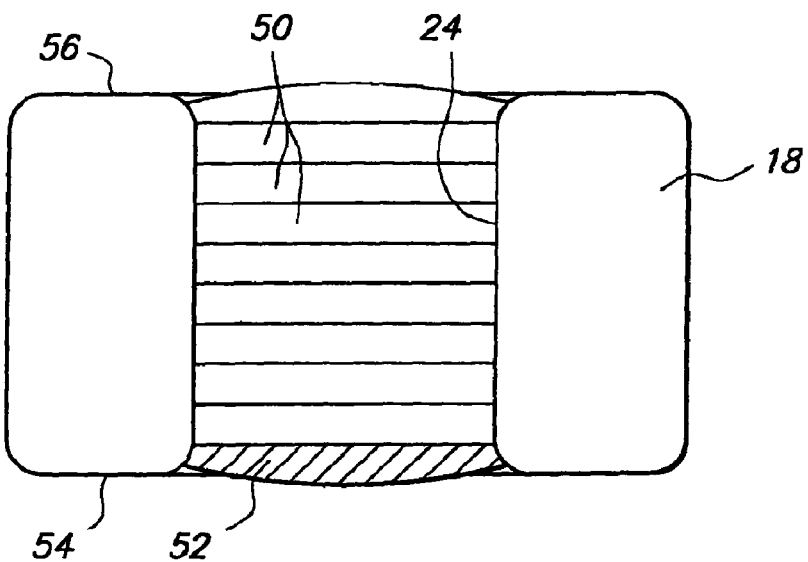
FIG. 10 is an enlarged cross section of an opening illustrating a beneficial agent and a barrier layer loaded into the opening in layers.

FIG. 10 shows a device in which the first layer 52 is loaded into a through opening 24 such that the inner surface of the layer is substantially co-planar with the inwardly facing surface 54 of the cylindrical device. The first layer 52 is comprised of a material called a barrier material which blocks or retards biodegradation of subsequent layers in the inwardly facing direction toward the vessel lumen, and/or blocks or retards diffusion of the beneficial agent in that direction. Biodegradation of other layers or beneficial agent diffusion can then proceed only in the direction of the outwardly facing surface 56 of the device, which is in direct contact with the targeted tissue of the vessel wall. The barrier layer 52 may also function to prevent hydration of inner layers of beneficial agent and thus prevent swelling of the inner layers when such layers are formed of hygroscopic materials. The barrier layer 52 may further be comprised of a biodegradable material that degrades at a much slower rate than the biodegradable material in the other layers, so that the opening will eventually be entirely cleared. Providing a barrier layer 52 in the most inwardly facing surface of a through-opening thus guarantees that the entire load of beneficial agent is delivered to the target area in the vessel wall. It should be noted that providing a barrier layer on the inwardly facing surface of a surface-coated stent without openings does not have the same effect; since the beneficial agent in such a coating cannot migrate through the metal stent to the target area on the outer surface, it simply remains trapped on the inner diameter of the device, again having no therapeutic effect.

Barrier layers can be used to control beneficial agent release kinetics in more sophisticated ways. A barrier layer 52 with a pre-determined degradation time could be used to deliberately terminate the beneficial agent therapy at a predetermined time, by exposing the underlying layers to more rapid bio-degradation from both sides. Barrier layers can also be formulated to be activated by a separate, systemically applied agent. Such systemically applied agent could change the porosity of the barrier layer and/or change the rate of bio-degradation of the barrier layer or the bulk beneficial agent carrier. In each case, release of the beneficial agent could be activated by the physician at will by delivery of the systemically applied agent. A further embodiment of physician activated therapy would utilize a beneficial agent encapsulated in micro-bubbles and loaded into device openings. Application of ultrasonic energy from an exterior of the body could be used to collapse the bubbles at a desired time, releasing the beneficial agent to diffuse to the outwardly facing surface of the reservoirs. These activation techniques can be used in conjunction with the release kinetics control techniques described herein to achieve a desired drug release profile that can be activated and/or terminated at selectable points in time.

Figure 11A:
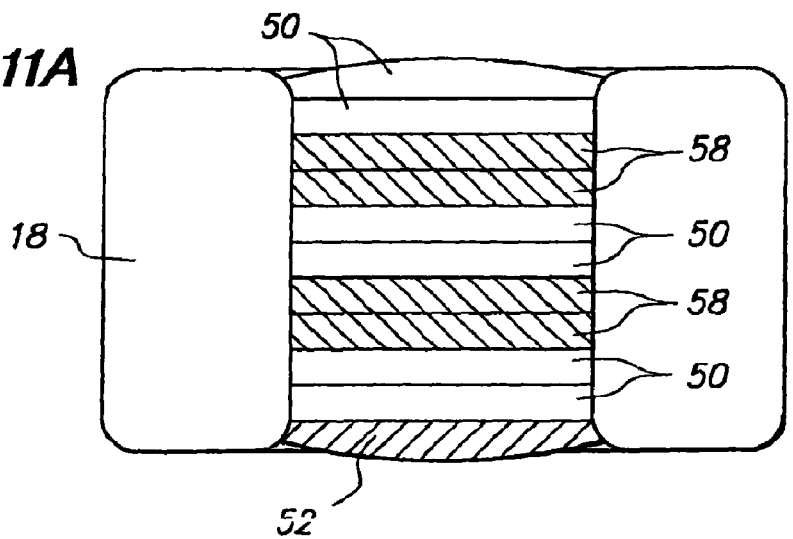
FIG. 11A is an enlarged cross section of an opening illustrating a beneficial agent, a biodegradable carrier, and a barrier layer loaded into the opening in layers.
Figure 11B:
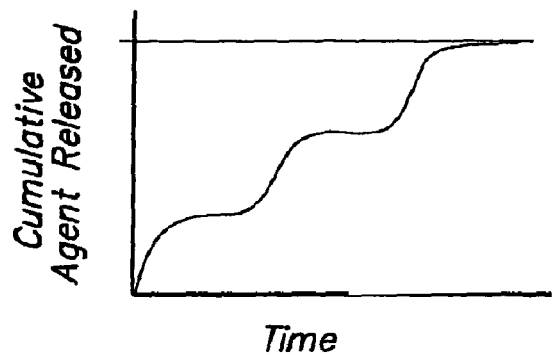
FIG. 11B is a graph of the release kinetics of the device of FIG. 11A.

FIG. 11A shows an arrangement of layers provided in a through opening in which layers 50 of a beneficial agent in a biodegradable carrier material, are alternated with layers 58 of the biodegradable carrier material alone, with no active agent loaded, and a barrier layer 52 is provided at the inwardly facing surface. As shown in the release kinetics plot of FIG. 11B, such an arrangement releases beneficial agent in three programmable bursts or waves achieving a stepped or pulsatile delivery profile. The use of carrier material layers without active agent creates the potential for synchronization of drug release with cellular biochemical processes for enhanced efficacy.

Figure 12:
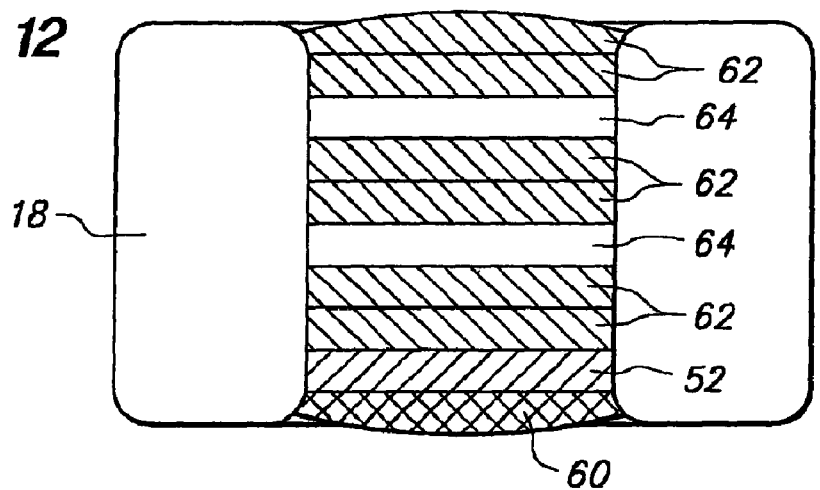
FIG. 12 is an enlarged cross section of an opening illustrating different beneficial agents, carrier, and barrier layers loaded into the opening.

Alternately, different layers could be comprised of different beneficial agents altogether, creating the ability to release different beneficial agents at different points in time, as shown in FIG. 12. For example, in FIG. 12, a layer 60 of anti-thrombotic agent could be deposited at the inwardly facing surface of the stent, followed by a barrier layer 52 and alternating layers of anti-proliferatives 62 and anti-inflammatories 64. This configuration could provide an initial release of anti-thrombotic agent into the bloodstream while simultaneously providing a gradual release of anti-proliferatives interspersed with programmed bursts of anti-inflammatory agents to the vessel wall. The configurations of these layers can be designed to achieve the agent delivery bursts at particular points in time coordinated with the body's various natural healing processes.

Figure 13:
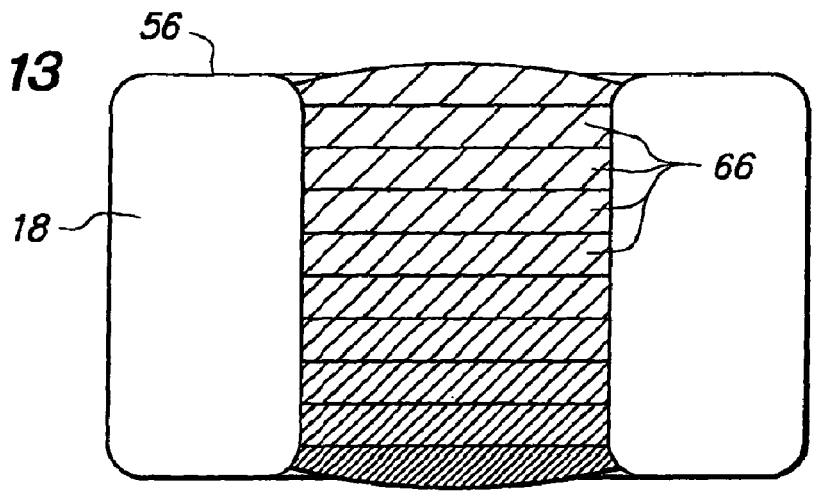
FIG. 13 is an enlarged cross section of an opening illustrating a beneficial agent loaded into the opening in layers of different concentrations.

A further alternative is illustrated in FIG. 13. Here the concentration of the same beneficial agent is varied from layer to layer, creating the ability to generate release profiles of arbitrary shape. Progressively increasing the concentration of agent in the layers 66 with increasing distance from the outwardly facing surface 56, for example, produces a release profile with a progressively increasing release rate, which would be impossible to produce in a thin surface coating.

Another general method for controlling beneficial agent release kinetics is to alter the beneficial agent flux by changing the surface area of drug elution sources as a function of time. This follows from Fick's First Law, which states that the instantaneous molecular flux is proportional to surface area, among other factors:

$$J = D\frac{\partial C}{\partial x} \Rightarrow \frac{\partial N}{\partial t} = AD\frac{\partial c}{\partial x}$$

Where $\partial N/\partial t$ is the number of molecules per unit time, A is the instantaneous drug eluting surface area, D is the diffusivity, and C is the concentration. The drug eluting surface area of a surface coated stent is simply the surface area of the stent itself. Since this area is fixed, this method of controlling release kinetics is not available to surface coated devices. Through openings, however, present several possibilities for varying surface area as a function of time.

Figure 14:
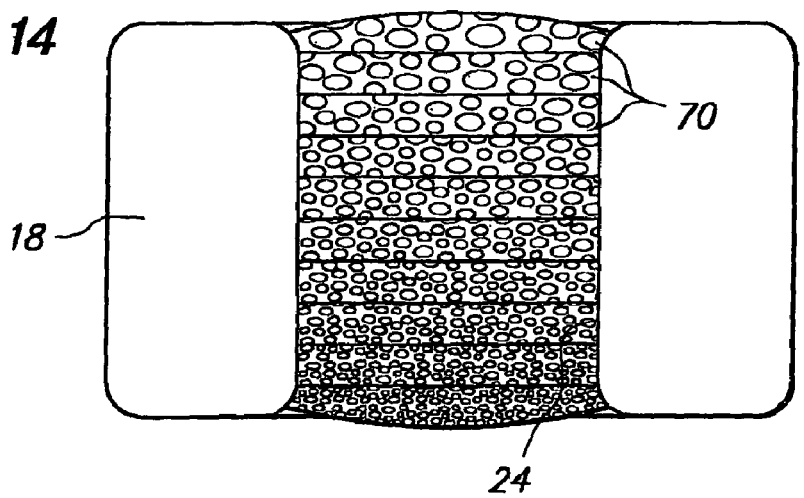
FIG. 14 is an enlarged cross section of an opening illustrating a beneficial agent loaded into the opening in layers of microspheres of different sizes.

In the embodiment of FIG. 14, beneficial agent is provided in the openings 24 in the form of microspheres, particles or the like. Individual layers 70 can then be created that contain these particles. Further, the particle size can be varied from layer to layer. For a given layer volume, smaller particle sizes increase the total particle surface area in that layer, which has the effect of varying the total surface area of the beneficial agent from layer to layer. Since the flux of drug molecules is proportional to surface area, the total drug flux can be adjusted from layer to layer by changing the particle size, and the net effect is control of release kinetics by varying particle sizes within layers.

Figure 15A:
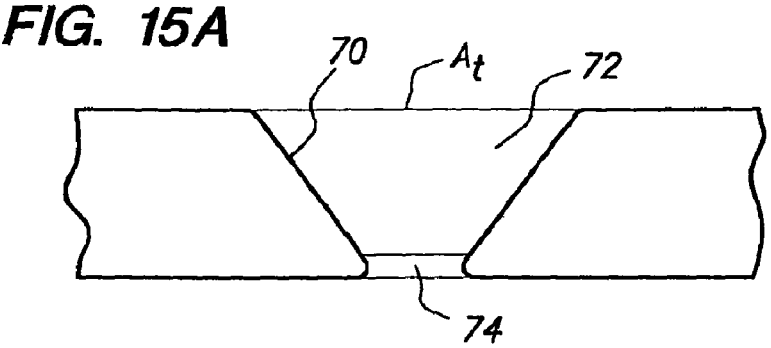
FIG. 15A is an enlarged cross section of a tapered opening illustrating a beneficial agent loaded into the opening.
Figure 15B:
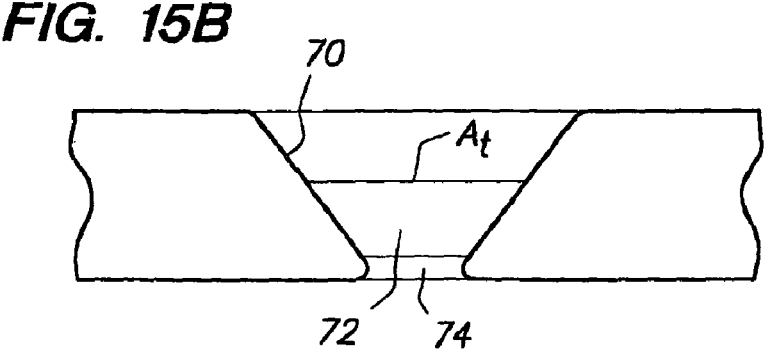
FIG. 15B is an enlarged cross section of the tapered opening of FIG. 15A with the beneficial agent partially degraded.
Figure 15C:
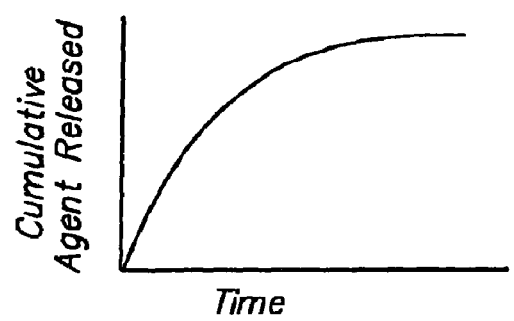
FIG. 15C is a graph of the release kinetics of the device of FIGS. 15A and 15B.

A second general method for varying drug eluting surface area as a function of time is to change the shape or cross-sectional area of the drug-bearing element along the axis of the opening. FIG. 15A shows an opening 70 having a conical shape cut into the material of the stent itself. The opening 70 may then be filled with beneficial agent 72 in layers as described above or in another manner. In this embodiment, a barrier layer 74 may be provided on the inwardly facing side of the opening 70 to prevent the beneficial agent 72 from passing into the blood stream. In this example, the drug eluting surface area $A_t$ would continuously diminish (from FIG. 15A to FIG. 15B) as the bio-degradable carrier material erodes, yielding the elution pattern of FIG. 15C.

Figure 16A:
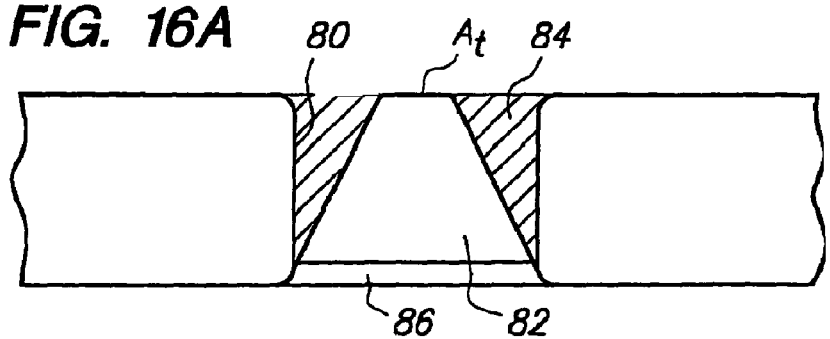
FIG. 16A is an enlarged cross section of an opening illustrating a beneficial agent loaded into the opening in a shape configured to achieve a desired agent delivery profile.
Figure 16B:
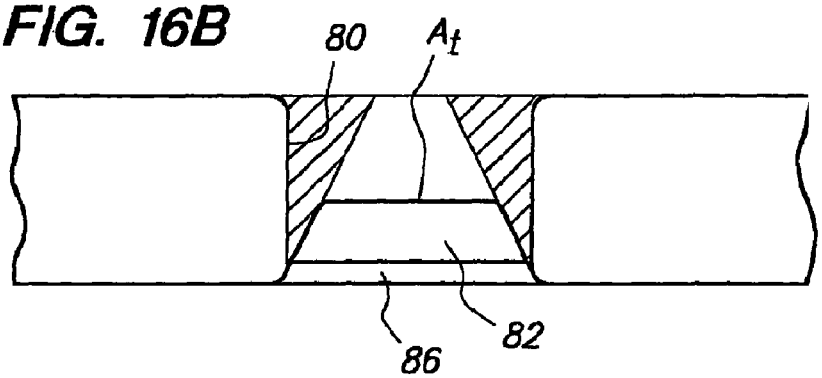
FIG. 16B is an enlarged cross section of the opening of FIG. 16A with the beneficial agent partially degraded.

FIG. 16A shows a simple cylindrical through-opening 80 in which a preformed, inverted cone 82 of beneficial agent has been inserted. The rest of the through opening 80 is then back-filled with a biodegradable substance 84 with a much slower rate of degradation or a non-biodegradable substance, and the inwardly facing opening of the through opening is sealed with a barrier layer 86. This technique yields the opposite behavior to the previous example. The drug-eluting surface area $A_t$ continuously increases with time between FIGS. 16A and 16B, yielding the elution pattern of FIG. 16C.

The changing cross section openings 70 of FIG. 15A and the non-biodegradable backfilling techniques of FIG. 16A may be combined with any of the layered agent embodiments of FIGS. 9-14 to achieve desired release profiles. For example, the embodiment of FIG. 15A may use the varying agent concentration layers of FIG. 13 to more accurately tailor a release curve to a desired profile.

Figure 17A:
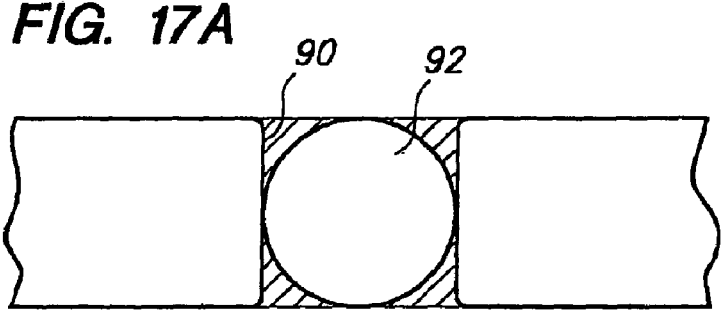
FIG. 17A is an enlarged cross section of an opening illustrating the beneficial agent loaded into the opening and a spherical shape.

The process of preforming the beneficial agent plug 82 to a special shape, inserting in a through opening, and back-filling with a second material can yield more complex release kinetics as well. FIG. 17A shows a through opening 90 in which a spherical beneficial agent plug 92 has been inserted. The resulting biodegradation of the sphere, in which the cross sectional surface area varies as a sinusoidal function of depth, produces a flux density which is roughly a sinusoidal function of time, FIG. 17B. Other results are of course possible with other profiles, but none of these more complex behaviors could be generated in a thin, fixed-area surface coating.

Figure 16C:
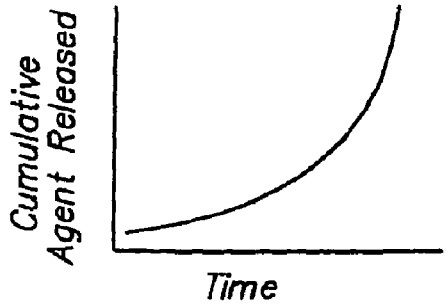
FIG. 16C is a graph of the release kinetics of the device of FIGS. 16A and 16B.
Figure 17B:
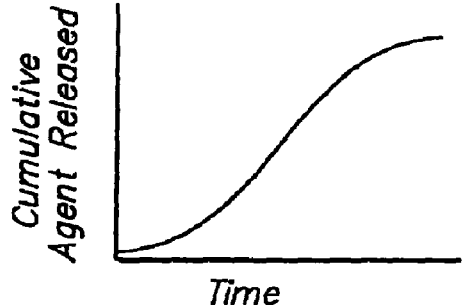
FIG. 17B is a graph of the release kinetics of the device of FIG. 17A.
Figure 18A:
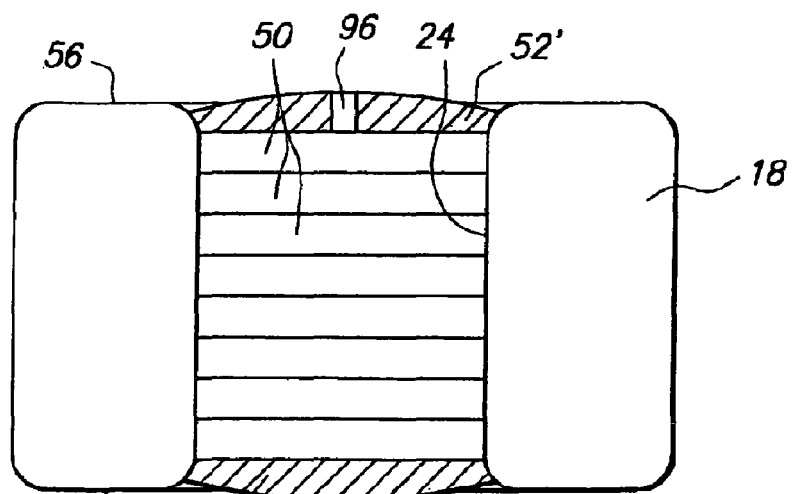
FIG. 18A is an enlarged cross section of an opening illustrating a plurality of beneficial agent layers and a barrier layer with an opening for achieving a desired agent delivery profile.
Figure 18B:
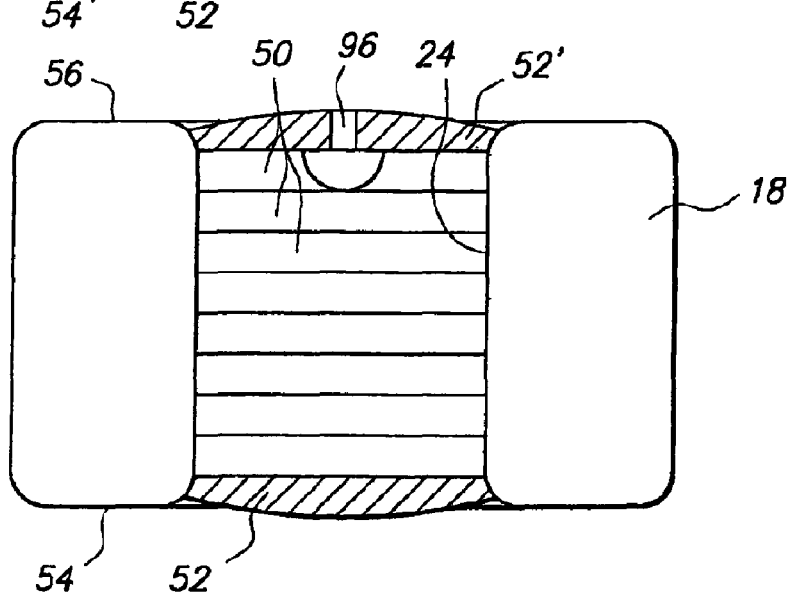
FIG. 18B is an enlarged cross section of the opening of FIG. 18A with the agent layers beginning to degraded.
Figure 18C:
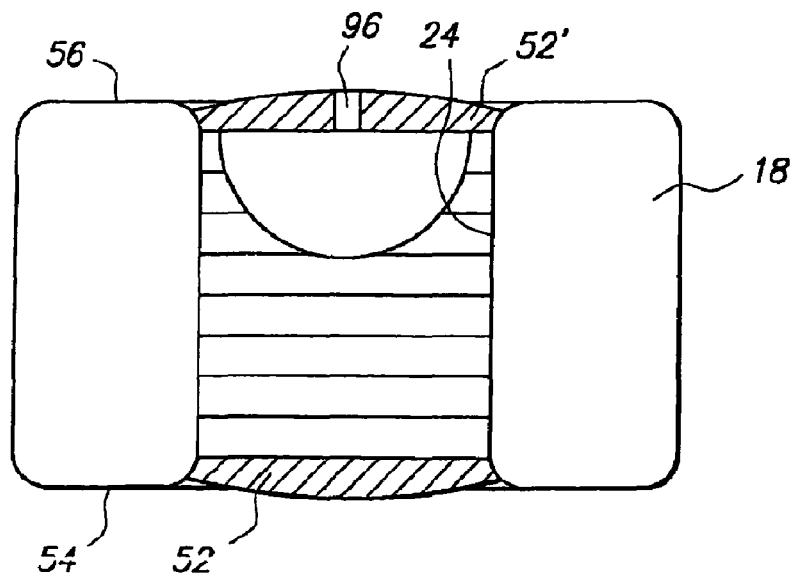
FIG. 18C is an enlarged cross section of the opening of FIG. 18A with the agent layers further degraded.

An alternate embodiment of FIGS. 18A-18C use a barrier layer 52' with an opening 96 to achieve the increasing agent release profile of FIG. 16C. As shown in FIG. 18A, the opening 24 is provided with an inner barrier layer 52 and multiple beneficial agent layers 50 as in the embodiment of FIG. 10.

An additional outer barrier layer 52' is provided with a small hole 96 for delivery of the agent to the vessel wall. As shown in FIGS. 18B and 18C, the beneficial agent containing layers 50 degrade in a hemispherical pattern resulting in increasing surface area for agent delivery over time and thus, an increasing agent release profile.

Figure 19:
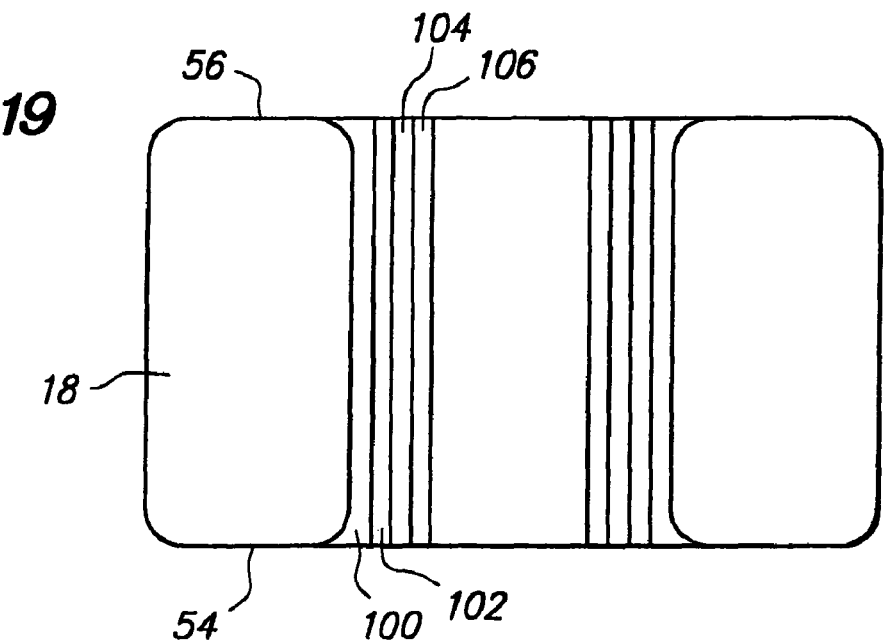
FIG. 19 is an enlarged cross section of an opening illustrating a plurality of cylindrical beneficial agent layers.

FIG. 19 illustrates an alternative embodiment in which an opening in the tissue supporting device is loaded with cylindrical layers of beneficial agent. According to one method of forming the device of FIG. 19, the entire device is coated with sequential layers 100, 102, 104, 106 of beneficial agent. The interior surface 54 and exterior surface 56 of the device are then stripped to remove the beneficial agent on these surfaces leaving the cylindrical layers of beneficial agent in the openings. In this embodiment, a central opening remains after the coating layers have been deposited which allows communication between the outer surface 56 and inner surface 54 of the tissue supporting device.

In the embodiment of FIG. 19, the cylindrical layers are eroded sequentially. This can be used for pulsatile delivery of different beneficial agents, delivery of different concentrations of beneficial agents, or delivery of the same agent. As shown in FIG. 19, the ends of the cylindrical layers 100, 102, 104, 106 are exposed. This results in a low level of erosion of the underlying layers during erosion of an exposed layer. Alternatively, the ends of the cylindrical layers may be covered by a barrier layer to prevent this low level continuous erosion. Erosion rates of the cylindrical layers may be further controlled by contouring the surfaces of the layers. For example, a ribbed or star-shaped pattern may be provided on the radially inner layers to provide a uniform surface area or uniform erosion rate between the radially inner layers and the radially outer layers. Contouring of the surfaces of layers may also be used in other embodiments to provide an additional variable for controlling the erosion rates.

Figure 20:
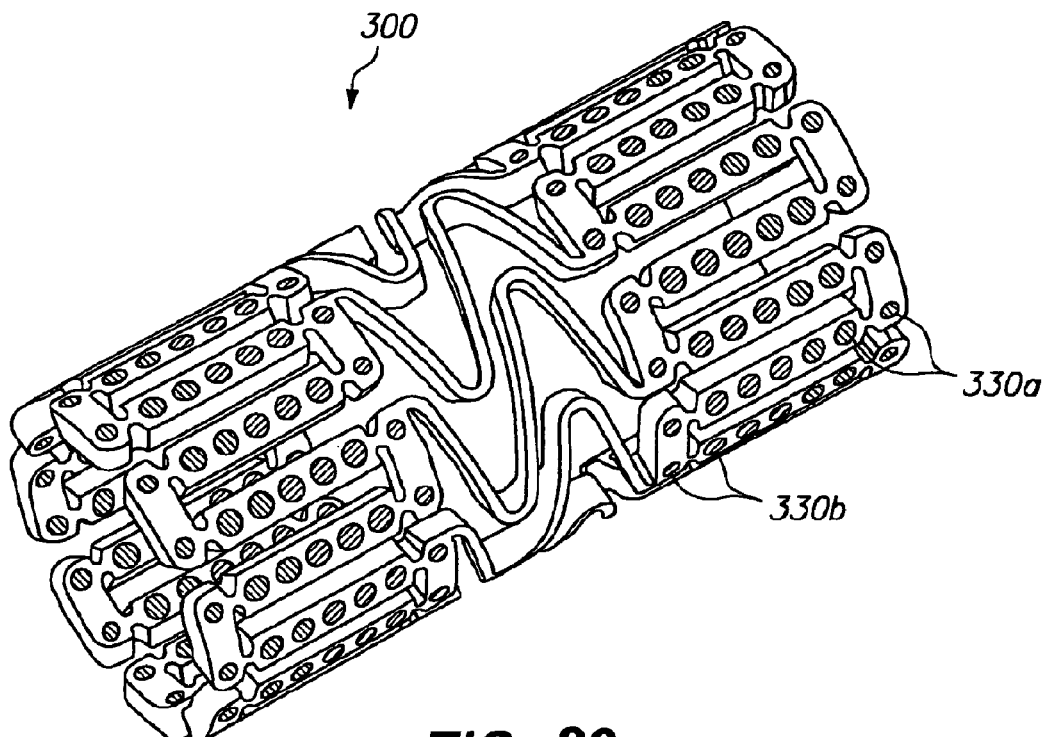
FIG. 20 is an isometric view of an expandable tissue supporting device with different beneficial agents in different holes.

FIG. 20 illustrates a further alternative embodiment of the invention in which different beneficial agents are positioned in different holes of an expandable medical device 300. A first beneficial agent is provided in holes 330a at the ends of the device and a second beneficial agent is provided in holes 330b at a central portion of the device. The beneficial agent may contain different drugs, the same drugs in different concentrations, or different variations of the same drug. The embodiment of FIG. 20 may be used to provide an expandable medical device 300 with either "hot ends" or "cool ends."

Preferably, each end portion of the device 300 which includes the holes 330a containing the first beneficial agent extends at least one hole and up to about 15 holes from the edge. This distance corresponds to about 0.005 to about 0.1 inches from the edge of an unexpanded device. The distance from the edge of the device 300 which includes the first beneficial agent is preferably about one section, where a section is defined between the bridging elements.

Different beneficial agents containing different drugs may be disposed in different openings in the stent. This allows the delivery of two or more beneficial agents from a single stent in any desired delivery pattern. Alternatively, different beneficial agents containing the same drug in different concentrations may be disposed in different openings. This allows the drug to be uniformly distributed to the tissue with a non-uniform device structure.

The two or more different beneficial agents provided in the devices described herein may contain (1) different drugs; (2) different concentrations of the same drug; (3) the same drug with different release kinetics, i.e., different matrix erosion rates; or (4) different forms of the same drug. Examples of different beneficial agents formulated containing the same drug with different release kinetics may use different carriers to achieve the elution profiles of different shapes. Some examples of different forms of the same drug include forms of a drug having varying hydrophilicity or lipophilicity.

In one example of the device 300 of FIG. 20, the holes 330a at the ends of the device are loaded with a first beneficial agent comprising a drug with a high lipophilicity while holes 330b at a central portion of the device are loaded with a second beneficial agent comprising the drug with a lower lipophilicity. The first high lipophilicity beneficial agent at the "hot ends" will diffuse more readily into the surrounding tissue reducing the edge effect restenosis.

The device 300 may have an abrupt transition line at which the beneficial agent changes from a first agent to a second agent. For example, all openings within 0.05 inches of the end of the device may contain the first agent while the remaining openings contain the second agent. Alternatively, the device may have a gradual transition between the first agent and the second agent. For example, a concentration of the drug in the openings can progressively increase (or decrease) toward the ends of the device. In another example, an amount of a first drug in the openings increases while an amount of a second drug in the openings decreases moving toward the ends of the device.

Figure 21:
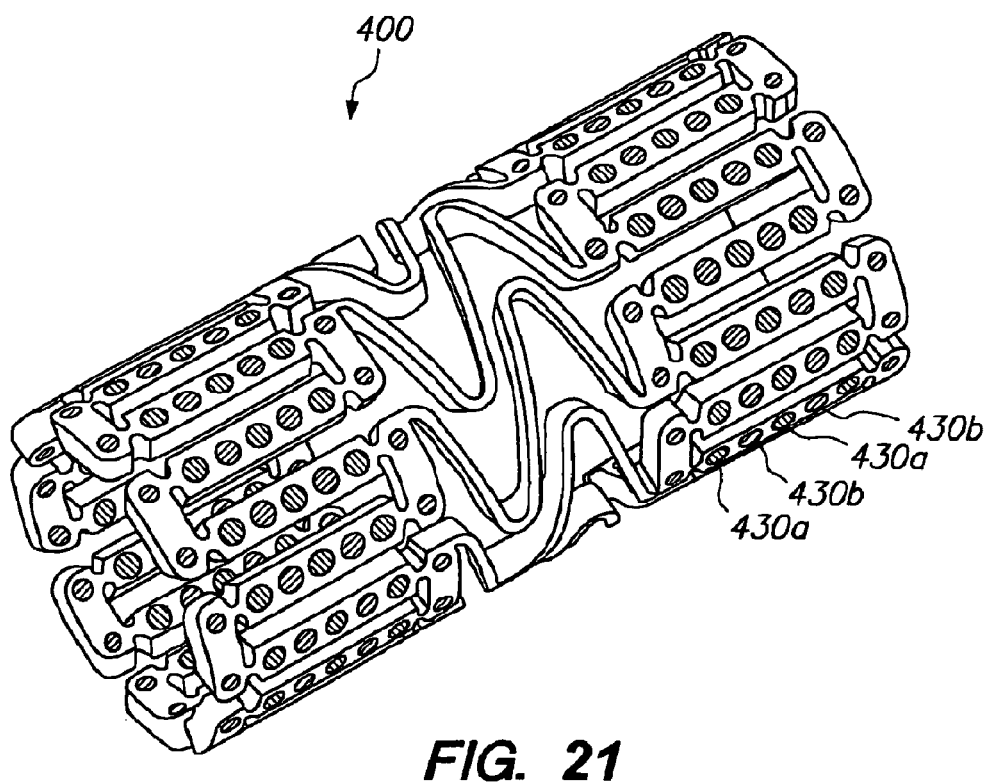
FIG. 21 is an isometric view of an expandable tissue supporting device with different beneficial agents in alternating holes.

FIG. 21 illustrates a further alternative embodiment of an expandable medical device 400 in which different beneficial agents are positioned in different openings 430a, 430b in the device in an alternating or interspersed manner. In this manner, multiple beneficial agents can be delivered to tissue over the entire area or a portion of the area supported by the device. This embodiment will be useful for delivery of multiple beneficial agents where combination of the multiple agents into a single composition for loading in the device is not possible due to interactions or stability problems between the beneficial agents.

In addition to the use of different beneficial agents in different openings to achieve different drug concentrations at different defined areas of tissue, the loading of different beneficial agents in different openings may be used to provide a more even spatial distribution of the beneficial agent delivered in instances where the expandable medical device has a non-uniform distribution of openings in the expanded configuration.

Figure 22:
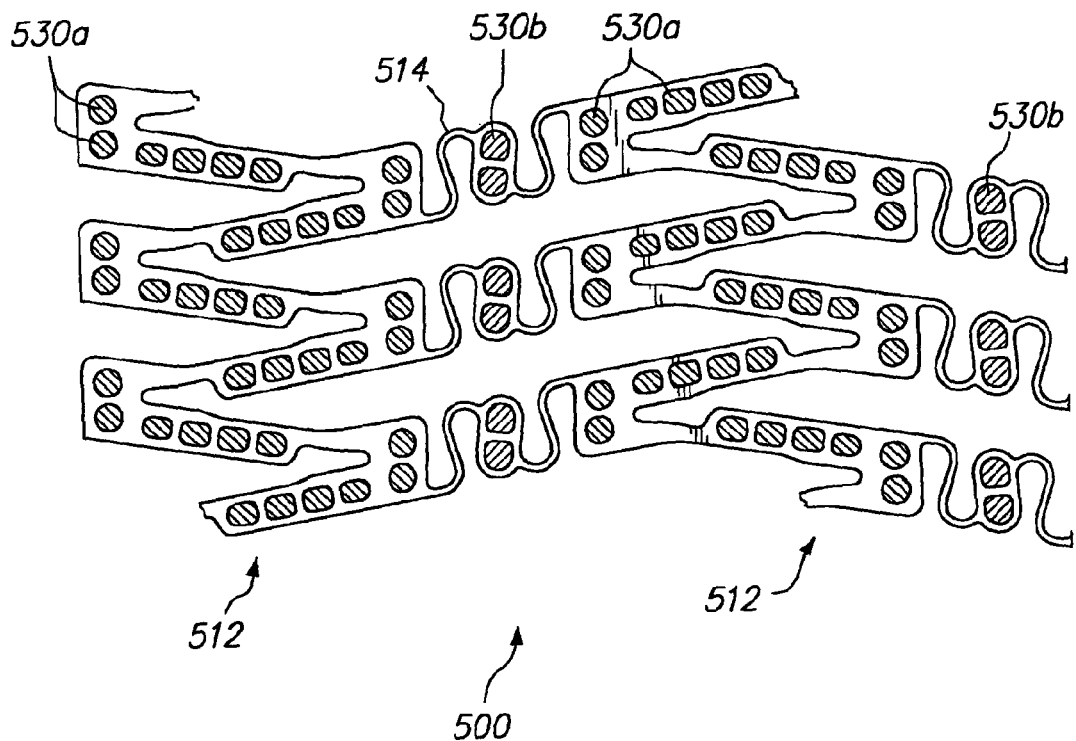
FIG. 22 is an enlarged side view of a portion of an expandable tissue supporting device with beneficial agent openings in the bridging elements.

For example, in many of the known expandable devices and for the device illustrated in FIG. 22 the coverage of the device 500 is greater at the cylindrical tube portions 512 of the device than at the bridging elements 514. Coverage is defined as the ratio of the device surface area to the area of the lumen in which the device is deployed. When a device with varying coverage is used to deliver a beneficial agent contained in openings in the device, the beneficial agent concentration delivered to the tissue adjacent the cylindrical tube portions 512 is greater that the beneficial agent delivered to the tissue adjacent the bridging elements 514. In order to address this longitudinal variation in device structure and other variations in device coverage which lead to uneven beneficial agent delivery concentrations, the concentration of the beneficial agent may be varied in the openings at portions of the device to achieve a more even distribution of the beneficial agent throughout the tissue. In the case of the embodiment of FIG. 22, the openings 530a in the tube portions 512 include a beneficial agent with a lower drug concentration than the openings 530b in the bridging elements 514. The uniformity of agent delivery may be achieved in a variety of manners including varying the drug concentration, the opening diameter or shape, the amount of agent in the opening (i.e., the percentage of the opening filed), the matrix material, or the form of the drug.

In addition to the delivery of different beneficial agents to the mural side of the expandable medical device for treatment of the vessel wall, beneficial agents may be delivered to the luminal side of the expandable medical device. Drugs which are delivered into the blood stream from the luminal side of the device can be located at a proximal end of the device or a distal end of the device.

The methods for loading different beneficial agents into different openings in an expandable medical device may include known techniques such as dipping and coating and also known piezoelectric micro-jetting techniques. Micro-injection devices may be computer controlled to deliver precise amounts of two or more liquid beneficial agents to precise locations on the expandable medical device in a known manner. For example, a dual agent jetting device may deliver two agents simultaneously or sequentially into the openings. When the beneficial agents are loaded into through openings in the expandable medical device, a luminal side of the through openings may be blocked during loading by a resilient mandrel allowing the beneficial agents to be delivered in liquid form, such as with a solvent. The beneficial agents may also be loaded by manual injection devices.

Therapeutic Layer Formulations

The therapeutic agent layers of the present invention are beneficial agents comprised of a matrix and at least one therapeutic agent. The term "matrix" or "biocompatible matrix" are used interchangeably to refer to a medium or material that, upon implantation in a subject, does not elicit a detrimental response sufficient to result in the rejection of the matrix. The matrix typically does not provide any therapeutic responses itself, though the matrix may contain or surround a therapeutic agent, a therapeutic agent, an activating agent or a deactivating agent, as defined herein. A matrix is also a medium that may simply provide support, structural integrity or structural barriers. The matrix may be polymeric, non-polymeric, hydrophobic, hydrophilic, lipophilic, amphiphilic, and the like.

The matrix of the therapeutic agent layers can be made from pharmaceutically acceptable polymers, such as those typically used in medical devices. The term "polymer" refers to molecules formed from the chemical union of two or more repeating units, called monomers. Accordingly, included within the term "polymer" may be, for example, dimers, trimers and oligomers. The polymer may be synthetic, naturally-occurring or semisynthetic. In preferred form, the term "polymer" refers to molecules which typically have a $M_w$ greater than about 3000 and preferably greater than about 10,000 and a $M_w$ that is less than about 10 million, preferably less than about a million and more preferably less than about 200,000. Examples of polymers include but are not limited to, poly-.alpha.-hydroxy acid esters such as, polylactic acid, polyglycolic acid, polylactic-co-glycolic acid, polylactic acid-co-caprolactone; polyethylene glycol and polyethylene oxide; polyvinyl pyrrolidone; polyorthoesters; polysaccharides and polysaccharide derivatives such as polyhyaluronic acid, polyalginic acid, chitin, chitosan, cellulose, hydroxyethylcellulose, hydroxypropylcellulose, carboxymethylcellulose; polypeptides, and proteins such as polylysine, polyglutamic acid, albumin; polyanhydrides; polyhydroxy alkonoates such as polyhydroxy valerate, polyhydroxy butyrate, and the like, and copolymers thereof. The polymers and copolymers can be prepared by methods well known in the art (see, for example, Rempp and Merril: Polymer Synthesis, 1998, John Wiley and Sons) in or can be used as purchased from Alkermes, in Cambridge, Mass. or Birmingham Polymer Inc., in Birmingham, Ala.

The preferred co-polymer for use in the present invention are poly(lactide-co-glycolide) (PLGA) polymers. The rate at which the polymer erodes is determined by the selection of the ratio of lactide to glycolide within the copolymer, the molecular weight of each polymer used, and the crystallinity of the polymers used. Bioerodible polymers may also be used to form barrier layers that erode at a rate that can be predetermined base on the composition and that contain no therapeutic agent.

Additives in Protective, Barrier, or Therapeutic Layer Formulations

Typical additives that may be included in a bioerodible matrix are well known to those skilled in the art (see Remington: The Science and Practice of Pharmacy, Gennaro, ed., Mack Publishing Co., Easton, Pa., 19th ed., 1995) and include but are not limited to pharmaceutically acceptable excipients, adjuvants, carriers, antioxidants, preservatives, buffers, antacids, emulsifiers, inert fillers, fragrances, thickeners, tackifiers, opacifiers, gelling agents, stabilizers, surfactants, emollients, coloring agents, and the like.

Typical formulations for therapeutic agents incorporated in these medical devices are well known to those skilled in the art and include but are not limited to solid particle dispersions, encapsulated agent dispersions, and emulsions, suspensions, liposomes or microparticles, wherein said liposome or microparticle comprise a homogeneous or heterogeneous mixture of the therapeutic agent.

The term "homogeneously disposed" refers to a component which is mixed uniformly in a matrix in such a manner that the component is macroscopically indistinguishable from the matrix itself. An example of a homogeneously disposed component is a drug formulation such as a microemulsion in which small beads of oil are dispersed uniformly in water.

The term "heterogeneously disposed" refers to a component that is mixed non-uniformly into a matrix in such a manner that the component is macroscopically distinguishable from the matrix itself. An example of a heterogeneously disposed component is a simple emulsion in which the beads of oil in the water are large enough to cause a turbidity to the solution and can be seen settling out of solution over time. Heterogeneously disposed compositions also include encapsulated formulations where a component, such as a protective layer, is layered onto or around a therapeutic agent or a therapeutic layer, forming a protective shell.

The amount of the drug that is present in the device, and that is required to achieve a therapeutic effect, depends on many factors, such as the minimum necessary dosage of the particular drug, the condition to be treated, the chosen location of the inserted device, the actual compound administered, the age, weight, and response of the individual patient, the severity of the patient's symptoms, and the like.

The appropriate dosage level of the therapeutic agent, for more traditional routes of administration, is known to one skilled in the art. These conventional dosage levels correspond to the upper range of dosage levels for compositions, including a physiologically active substance and traditional penetration enhancer. However, because the delivery of the active substance occurs at the site where the drug is required, dosage levels significantly lower than a conventional dosage level may be used with success. Ultimately, the percentage of therapeutic agent in the composition is determined by the required effective dosage, the therapeutic activity of the particular formulation, and the desired release profile. In general, the active substance will be present in the composition in an amount from about 0.0001% to about 99%, more preferably about 0.01% to about 80% by weight of the total composition depending upon the particular substance employed. However, generally the amount will range from about 0.01% to about 75% by weight of the total composition, with levels of from about 25% to about 75% being preferred.

Protective and Barrier Layer Formulations

The protective and barrier layers of the present invention are beneficial agents comprised of a bioerodible matrix and optionally contain additional additives, therapeutic agents, activating agents, deactivating agents, and the like. Either a property of the chosen material of the protective or barrier layer, or a chemical embedded in the protective or barrier layer provides protection from deactivating processes or conditions for at least one therapeutic agent. In addition to the polymer materials described above, the protective or barrier layer may also be comprised of pharmaceutically acceptable lipids or lipid derivatives, which are well known in the art and include but are not limited to fatty acids, fatty acid esters, lysolipids, phosphocholines, (Avanti Polar Lipids, Alabaster, Ala.), including 1-alkyl-2-acetoyl-sn-gl-ycero 3-phosphocholines, and 1-alkyl-2-hydroxy-sn-glycero 3-phosphocholines; phosphatidylcholine with both saturated and unsaturated lipids, including dioleoylphosphatidylcholine; dimyristoyl-phosphatidylcholine; dipentadecanoylphosphatidylcholine; dilauroylphosphatidyl-choline; dipalmitoylphosphatidylcholine (DPPC); distearoylphosphatidylcholine (DSPC); and diarachidonylphosphatidylcholin-e (DAPC); phosphatidyl-ethanolamines, such as dioleoylphosphatidylethanola-mine, dipahnitoyl-phosphatidylethanola-mine (DPPE) and distearoylphosphatidylefhanolamine (D SPE); phosphatidylserine; phosphatidylglycerols, including distearoylphosphatidylglycerol (DSPG); phosphatidylinositol; sphingolipids such as sphingomyelin; glucolipids; sulfatides; glycosphingolipids; phosphatidic acids, such as dipahmitoylphosphatidic acid (DPPA) and distearoylphosphatidic acid (DSPA); palmitic acid; stearic acid; arachidonic acid; oleic acid; lipids bearing polymers, such as chitin, hyaluronic acid, polyvinylpyrrolidone or polyethylene glycol (PEG), also referred to herein as "pegylated lipids", with preferred lipids bearing polymers including DPPE-PEG (DPPE-PEG), which refers to the lipid DPPE having a PEG polymer attached thereto, including, for example, DPPE-PEG5000, which refers to DPPE having attached thereto a PEG polymer having a mean average molecular weight of about 5000; lipids bearing sulfonated mono-, di-, oligo- or polysaccharides; cholesterol, cholesterol sulfate and cholesterol hemisuccinate; tocopherol hemisuccinate; lipids with ether and ester-linked fatty acids; polymerized lipids (a wide variety of which are well known in the art); diacetyl phosphate; dicetyl phosphate; stearylamine; cardiolipin; phospholipids with short chain fatty acids of about 6 to about 8 carbons in length; synthetic phospholipids with asymmetric acyl chains, such as, for example, one acyl chain of about 6 carbons and another acyl chain of about 12 carbons; ceramides; non-ionic liposomes including niosomes such as polyoxyethylene fatty acid esters, polyoxyethylene fatty alcohols, polyoxyethylene fatty alcohol ethers, polyoxyethylated sorbitan fatty acid esters, glycerol polyethylene glycol oxystearate, glycerol polyethylene glycol ricinoleate, ethoxylated soybean sterols, ethoxylated castor oil, polyoxyethylene-polyoxypropylene polymers, and polyoxyethylene fatty acid stearates; sterol aliphatic acid esters including cholesterol sulfate, cholesterol butyrate, cholesterol iso-butyrate, cholesterol palmitate, cholesterol stearate, lanosterol acetate, ergosterol palmitate, and phytosterol n-butyrate; sterol esters of sugar acids including cholesterol glucuronide, lanosterol glucuronide, 7-dehydrocholesterol glucuronide, ergosterol glucuronide, cholesterol gluconate, lanosterol gluconate, and ergosterol gluconate; esters of sugar acids and alcohols including lauryl glucuronide, stearoyl glucuronide, myristoyl glucuronide, lauryl gluconate, myristoyl gluconate, and stearoyl gluconate; esters of sugars and aliphatic acids including sucrose acetate isobutyrate (SAIB), sucrose laurate, fructose laurate, sucrose palritate, sucrose stearate, glucuronic acid, gluconic acid and polyuronic acid; saponins including sarsasapogenin, smilagenin, hederagenin, oleanolic acid, and digitoxigenin; glycerol dilaurate, glycerol trilaurate, glycerol monolaurate, glycerol dipalmitate, glycerol and glycerol esters including glycerol tripalmitate, glycerol monopalmitate, glycerol distearate, glycerol tristearate, glycerol monostearate, glycerol monomyristate, glycerol dimyristate, glycerol trimyristate; long chain alcohols including n-decyl alcohol, lauryl alcohol, myristyl alcohol, cetyl alcohol, and n-octadecyl alcohol; 1,2-dioleoyl-sn-glycerol; 1,2-dipalmitoyl-sn-3-succinylglycerol; 1,3-dipalmitoyl-2-succinylglycerol; 1-hexadecyl-2-palmitoylglycerophospho-ethanolamine and palmitoylhomocysteine, and/or combinations thereof.

If desired, a cationic lipid may be used, such as, for example, N-[1-(2,3-dioleoyloxy)propyl]-N,N,N-trimethylammonium chloride (DOTMA), 1,2-dioleoyloxy-3-(trimethylammonio)propane (DOTAP); and 1,2-dioleoyl-3-(4'-trimethylammonio)butanoyl-sn-glycerol (DOTB). If a cationic lipid is employed in the lipid compositions, the molar ratio of cationic lipid to non-cationic lipid may be, for example, from about 1:1000 to about 1:100. Preferably, the molar ratio of cationic lipid to non-cationic lipid may be from about 1:2 to about 1:10, with a ratio of from about 1:1 to about 1:2.5 being preferred. Even more preferably, the molar ratio of cationic lipid to non-cationic lipid may be about 1:1. These lipid materials are well known in the art and can be used as purchased from Avanti, Burnaby, B.C. Canada.

The preferred lipids for use in the present invention are phosphatidyl-choline, phosphatidylethanolamine, phosphatidylserine, sphingomyelin as well as synthetic phospholipids such as dimyristoyl phosphatidylcholine, dipalmitoyl phosphatidylcholine, distearoyl phosphatidylcholine, distearoyl phosphatidyl-glycerol, dipalmitoyl phosphatidylglycerol, dimyristoyl phosphatidylserine, distearoyl phosphatidylserine and dipalmitoyl phosphatidylserine.

The rate at which the bioerodible matrix erodes is determined by the choice of lipid, the molecular weight, and the ratio of the chosen materials. The protective or barrier layer can erode by either chemical or physical erosion mechanisms. If the layer erodes by a physical mechanism, the layer is typically a thin film from about 0.1 µm to about 3 µm of a non-polymeric material embedded between two polymeric layers. In this instance, the structural integrity of the protective or barrier layer is maintained by the presence of both of these polymeric layers. When the polymeric material closest to the luminal surface erodes away, the protective or barrier layer breaks apart by the physical forces exerted on it from the remaining polymeric layer. In another embodiment, the protective or barrier layer is eroded by chemical interactions, dissolution in water, hydrolysis, or reaction with enzymes.

One function of the protective or barrier layer is to protect one or more therapeutic agents from deactivating or degrading conditions. The protection may come from the properties of the material when, for example, a hydrophobic protective or barrier layer would protect a water sensitive agent from water by resisting the influx of moisture. The protective or barrier layer may also act as a physical barrier. For example, a protective or barrier layer comprised of a hydrogel may allow water to be absorbed by the gel, and allow any agents contained within the gel to diffuse out of the gel into the reaction environment. The hydrogel, however, would prevent enzymes from penetrating the layer, thereby protecting any agents contained within from the enzyme. The term "hydrogel" refers to cross-linked polymeric material in which the liquid component is water. Hydrogels may be prepared by cross-linking certain polymers and lipids disclosed herein.

Finally the protective or barrier layer does not have to act as a barrier. The protective or barrier layer may protect a therapeutic agent by releasing an agent, such as an activating agent or a deactivating agent, into the reaction environment prior to the release of the therapeutic agent.

A therapeutic agent may be incorporated directly in the protective or barrier layer. The therapeutic agent can be heterogeneously or homogeneously dispersed in the protective or barrier layer. The therapeutic agent can be a drug, or a drug formulated into a microcapsule, niosome, liposome, microbubble, microsphere, or the like. In addition, the protective or barrier layer may contain more than one therapeutic agent. For example, a water sensitive drugs, such as a limus, or any other drug that must be administered through intravenous, intramuscular, or subcutaneously, could be incorporated in a hydrophobic matrix such as SAIB, or fatty acid ester.

A therapeutic agent may also be disposed in a therapeutic agent layer, separate from the protective or barrier layer. In this case the protective or barrier layer may be adjacent to the therapeutic agent layer and may serve to prevent or retard processes that would degrade or deactivate the therapeutic agent until the protective or barrier layer has substantially eroded. In this instance the protective or barrier layer is a barrier between a therapeutic layer and the reaction environment. This barrier may be a hydrophobic barrier that resists water absorption. The hydrophobic barrier would be used in conjunction with water-sensitive drugs as described above. Alternatively, the protective or barrier layer may be a hydrogel that resists the absorbance of enzymes. An enzyme resistant barrier would used to protect an drug such as a DNA, RNA, peptide or protein based therapeutic agent.

The protective or barrier layer may optionally include activating and deactivating agents for the purpose of preparing the reaction environment for the subsequent release of a therapeutic agent. These activating and deactivating agents are well known to those skilled in the art and include but are not limited to antacids, buffers, enzyme inhibitors, hydrophobic additives, and adjuvants. For example, $Mg(OH)_2$ in particles of about 0.5 µm to about 5 µm more preferably, about 1 µm incorporated in a PLGA polymer layer could be used in conjunction with any acid sensitive drug. An example of an activating agent is chymotrypsin, which may be incorporated in polyvinyl pyrrolidone layer. The chymotrypsin could be used to convert a pro-drug to an active drug.

While the invention has been described in detail with reference to exemplary embodiments thereof, it will be apparent to one skilled in the art that various changes can be made, and equivalents employed, without departing from the scope of the invention. The foregoing description of the preferred embodiments of the invention has been presented for purposes of illustration and description. It is not intended to be exhaustive or to limit the invention to the precise form disclosed, and modifications and variations are possible in light of the above teachings or may be acquired from practice of the invention. The embodiments were chosen and described in order to explain the principles of the invention and its practical application to enable one skilled in the art to utilize the invention in various embodiments as are suited to the particular use contemplated. It is intended that the scope of the invention be defined by the claims appended hereto, and their equivalents. The entirety of each of the aforementioned documents is incorporated by reference herein.

What is claimed is:

1. A method of forming an implantable medical device configured to release at least one therapeutic agent therefrom, wherein the therapeutic agent is disposed in a matrix affixed to the body of the implantable medical device, the body includes at least one recess, and wherein the concentration of the at least one therapeutic agent in the matrix varies as a continuous gradient relative to a surface of the body of the implantable medical device, the method comprising: forming a first homogeneous solution comprising an amount of the at least one therapeutic agent mixed with a polymeric binder; introducing the first homogeneous solution into the at least one recess in the body of the implantable medical device; solidifying the first homogeneous solution, thereby forming a first portion of the matrix; forming a second homogeneous solution comprising an amount of the at least one therapeutic agent mixed with the polymeric binder; applying the second homogeneous solution to the first portion of the matrix, thereby at least partially liquefying the first portion of the matrix; and solidifying the second homogeneous solution, thereby forming a second portion of the matrix, wherein the concentration of the at least one therapeutic agent in the matrix is different in the first and second portions of the matrix.

2. The method of claim 1, wherein the first and second homogenous solutions include a solvent and the first and second homogenous solutions are solidified by evaporation of the solvent.

3. The method of claim 1, further comprising: applying successive homogeneous solutions to the matrix; and solidifying the successive homogeneous solutions, thereby forming additional portions of the matrix, wherein the concentration of the therapeutic agent in the matrix is different in the successive portions of the matrix.

4. The method of claim 1, further comprising: applying a solution of a barrier material prior to introducing the first homogenous solution, the barrier material forming a barrier to the passage of the therapeutic agent in the first homogenous solution to one side of the body of the implantable medical device.

5. The method of claim 4, further comprising: applying successive homogeneous solutions to the matrix; and solidifying the successive homogeneous solutions, thereby forming additional portions of the matrix, wherein the concentration of the at least one therapeutic agent in the matrix is different in the successive portions of the matrix.

* * * * *